US012728294B2

(12) United States Patent
Xu et al.

(10) Patent No.: US 12,728,294 B2
(45) Date of Patent: Sep. 8, 2026

(54) FOCUSED ULTRASOUND TREATMENT SYSTEM BASED ON ULTRASOUND IMAGING

(71) Applicant: FUDAN UNIVERSITY, Shanghai (CN)

(72) Inventors: Kailiang Xu, Shanghai (CN); Yapeng Fu, Shanghai (CN); Junjin Yu, Shanghai (CN); Xingyi Guo, Shanghai (CN); Shaoyuan Yan, Shanghai (CN); Dean Ta, Shanghai (CN); Weiqi Wang, Shanghai (CN)

(73) Assignee: FUDAN UNIVERSITY, Shanghai (CN)

( * ) Notice: Subject to any disclaimer, the term of this patent is extended or adjusted under 35 U.S.C. 154(b) by 239 days.

(21) Appl. No.: 18/685,959

(22) PCT Filed: Aug. 23, 2022

(86) PCT No.: PCT/CN2022/114344
§ 371 (c)(1),
(2) Date: Feb. 23, 2024

(87) PCT Pub. No.: WO2023/025165
PCT Pub. Date: Mar. 2, 2023

(65) Prior Publication Data

US 2024/0366969 A1 Nov. 7, 2024

(30) Foreign Application Priority Data

Aug. 23, 2021 (CN) ......................... 202110970062.5

(51) Int. Cl.
*A61N 7/02* (2006.01)
*A61B 8/00* (2006.01)
(Continued)

(52) U.S. Cl.
CPC .................. *A61N 7/02* (2013.01); *A61B 8/06* (2013.01); *A61B 8/481* (2013.01); *A61B 8/488* (2013.01);
(Continued)

(58) Field of Classification Search
None
See application file for complete search history.

(56) References Cited

U.S. PATENT DOCUMENTS 6,176,832 B1 * 1/2001 Habu .................. A61B 5/0285 600/490
2011/0251607 A1 * 10/2011 Kruecker ........... A61B 18/1815 600/407
(Continued)

FOREIGN PATENT DOCUMENTS

CN 102232856 A 11/2011
CN 108969914 A 12/2018
(Continued)

*Primary Examiner* — Jonathan Cwern
(74) *Attorney, Agent, or Firm* — NKL Law; Bin Lu; Allen Xue

(57) ABSTRACT

A focused ultrasound treatment system has: a focused ultrasound unit configured to emit focused ultrasound waves to a focal region to perform treatment; an ultrasound imaging unit configured to, after treatment emit imaging ultrasonic waves to an imaging region and receive corresponding echoes, and image a corresponding vascular blood flow image on the basis of the echo; a region planning and parameter adjustment unit configured to re-delineate a focal region on the basis of the vascular blood flow image and to re-adjust a treatment parameter of the focused ultrasound unit so as to be used to next treat the re-delineated focal region. The imaging region contains the focal region.

14 Claims, 21 Drawing Sheets

(51) Int. Cl.
*A61B 8/06* (2006.01)
*A61N 7/00* (2006.01)

(52) U.S. Cl.
CPC .......... *A61B 8/5246* (2013.01); *A61B 8/5261* (2013.01); *A61B 8/5269* (2013.01); *A61N 2007/0052* (2013.01)

(56) References Cited

U.S. PATENT DOCUMENTS

| | | | | |
|---|---|---|---|---|
| 2012/0283564 | A1* | 11/2012 | Ebbini | A61B 8/085 600/443 |
| 2015/0073400 | A1* | 3/2015 | Sverdlik | A61N 7/022 606/28 |
| 2015/0294497 | A1* | 10/2015 | Ng | A61B 8/483 382/128 |
| 2016/0143617 | A1* | 5/2016 | Ebbini | G01S 15/8915 600/447 |
| 2018/0369065 | A1* | 12/2018 | Siedenburg | A61B 8/04 |
| 2019/0298300 | A1* | 10/2019 | Lu | A61B 8/463 |
| 2020/0107817 | A1* | 4/2020 | Provost | A61B 8/481 |
| 2020/0118274 | A1* | 4/2020 | Saito | A61B 1/000094 |

FOREIGN PATENT DOCUMENTS

| | | | |
|---|---|---|---|
| CN | 209422796 | U | 9/2019 |
| CN | 110465008 | A | 11/2019 |
| CN | 111184949 | A | 5/2020 |

* cited by examiner

FOCUSED ULTRASOUND TREATMENT SYSTEM BASED ON ULTRASOUND IMAGING

CROSS REFERENCE TO RELATED APPLICATIONS

This patent application claims the benefit of PCT Application PCT/CN2022/114344 filed Aug. 23, 2022, which claims the benefit of Chinese patent application 202110970062.5 filed Aug. 23, 2021, each of which is incorporated by reference herein in its entirety.

TECHNICAL FIELD

The present invention generally relates to the field of ultrasound imaging treatment, and particularly to focused ultrasound treatment technology based on ultrasound imaging.

BACKGROUND

High-intensity focused ultrasound (HIFU) technology is an ultrasound treatment technique used for the treatment of tumors, masses, nodules, polyps, and other tissue abnormalities, offering advantages such as non-invasiveness, no radiation, and relative cost-effectiveness. High-intensity focused ultrasound utilizes characteristics like strong ultrasound penetration and good directionality to concentrate sonic energy on the target region, causing coagulative necrosis in the target tissue through thermal and mechanical effects to achieve the treatment objective.

Currently, high-intensity focused ultrasound technology has been widely applied in the treatment of conditions such as fibroids, tumors, Parkinson's disease, and hereditary tremors. Techniques such as magnetic resonance imaging (MRI), positron emission tomography (PET), and computed tomography (CT) are commonly used to locate the treatment region and monitor the treatment effect. However, there are still significant challenges in clinical use, including difficulties in dynamically monitoring the treatment and imaging regions, limited imaging speed, lack of portability, inability to present the treatment region in real time and plan the treatment process, and high detection costs.

SUMMARY

The objective of this invention is to provide a focused ultrasound treatment system based on ultrasound imaging, achieving dynamic and precise treatment of lesions under the coordination of the focused ultrasound unit and the ultrasound imaging unit.

The invention discloses a focused ultrasound treatment system based on ultrasound imaging, comprising:

a focused ultrasound unit, configured to emit focused ultrasound waves to a lesion region for treatment;

an ultrasound imaging unit, configured to, after the treatment, emit imaging ultrasound waves to an imaging region and receive corresponding echoes, and based on the echoes, form a corresponding vascular blood flow image; and a region planning and parameter adjustment unit, configured to, based on the vascular blood flow image, re-delineate the lesion region and re-adjust the treatment parameters of the focused ultrasound unit for a next treatment of the re-delineated lesion region, wherein the imaging region comprises the lesion region.

Optionally, the ultrasound imaging unit emits ultrasound waves at a frame rate of ≥200 frames/s, and images at a frame rate of ≥50 frames/s; the vascular blood flow image is a microvascular blood flow image, with a microvascular blood flow imaging resolution of ≤the wavelength of the emitted ultrasound waves.

Optionally, the region planning and parameter adjustment unit is further configured to determine the corresponding vascular blood flow network contour and the respective vascular density index, blood flow velocity index, and blood flow volume index based on the vascular blood flow image, and to re-delineate the lesion region according to the vascular blood flow network contour and to score the lesion state of the re-delineated lesion region according to one or more of the vascular density index, blood flow velocity index, and blood flow volume index, compare the scoring result with an expected result, and re-adjust the treatment parameters of the focused ultrasound unit based on the comparison result for the next treatment of the re-delineated lesion region.

Optionally, the region planning and parameter adjustment unit is further configured to determine the vascular blood flow network contour and blood flow direction within the re-delineated lesion region according to the vascular blood flow image, and to plan the treatment route based on the vascular blood flow network contour and the blood flow direction for the next treatment of the re-delineated lesion region by the focused ultrasound unit.

Optionally, the system further comprises an image input unit and an image fusion unit; wherein, the image input unit is configured to acquire registration reference images and output them to the image fusion unit; the image fusion unit is configured to register and fuse the vascular blood flow image and the registration reference image to obtain a registered and fused image; and, the region planning and parameter adjustment unit is further configured to, based on the registered and fused image, re-delineate the lesion region and re-adjust the treatment parameters of the focused ultrasound unit for the next treatment of the re-delineated lesion region.

Optionally, the region planning and parameter adjustment unit is further configured to determine the corresponding vascular blood flow network contour and the respective vascular density index, blood flow velocity index, and blood flow volume index based on the registered and fused image, and to re-delineate the lesion region according to the vascular blood flow network contour and to score the lesion state of the re-delineated lesion region according to one or more of the vascular density index, blood flow velocity index, and blood flow volume index, compare the scoring result with an expected result, and re-adjust the treatment parameters of the focused ultrasound unit based on the comparison result for the next treatment of the re-delineated lesion region.

Optionally, the region planning and parameter adjustment unit is further configured to binarize the vascular blood flow image to obtain the vascular blood flow network contour;

the region planning and parameter adjustment unit is further configured to, based on a super-resolution vascular blood flow image, calculate the blood flow velocity index by using the quotient of the length of the tracer trajectory and the time taken by the tracer to move along the trajectory, or to directly obtain the blood flow velocity index from a power Doppler vascular blood flow image or a color Doppler vascular blood flow image;

the region planning and parameter adjustment unit is further configured to, based on the vascular blood flow network contour, determine central position points S(x, y) of each vascular blood flow within the vascular blood flow network contour and obtain the vascular blood flow radius r(x, y) at each central position point S(x, y), and calculate the blood flow volume index using the formula $Q=\Sigma_{S(x,y)}v(x, y)*\pi r(x, y)^2$;

the region planning and parameter adjustment unit is further configured to calculate the vascular density index by using the quotient of the region of the vascular blood flow image formed by the vascular blood flow network contour and the current imaging image region, or the quotient of the volume of the vascular blood flow image formed by the vascular blood flow network contour and the current imaging space volume.

Optionally, the region planning and parameter adjustment unit is further configured to determine the vascular blood flow network contour and the blood flow direction within the re-delineated lesion region based on the registered and fused image, and to plan the treatment route based on the vascular blood flow network contour and the blood flow direction for the next treatment of the re-delineated lesion region by the focused ultrasound unit.

Optionally, the ultrasound imaging unit is further configured to, after the treatment, emit imaging ultrasound waves to the imaging region and receive corresponding echoes, and based on the echoes, form a corresponding B-mode image, and obtain the vascular blood flow image based on the B-mode image.

Optionally, the ultrasound imaging unit is further configured to perform clutter filtering on the B-mode image, followed by positioning and tracking of either red blood cells or tracers within the clutter-filtered B-mode image, and based on the results of positioning and tracking, reconstruct the vascular blood flow image within the B-mode image to obtain a corresponding super-resolution vascular blood flow image, wherein the tracer is introduced into the vascular blood flow via venous injection after each treatment.

Optionally, the ultrasound imaging unit is further configured to perform clutter filtering, orthogonal demodulation, and frequency shift analysis on the B-mode image to obtain a corresponding power Doppler vascular blood flow image or a color Doppler vascular blood flow image.

Optionally, a cycle of sequential operations of the focused ultrasound unit, the ultrasound imaging unit, and the region planning and parameter adjustment unit constitutes a treatment cycle, and each treatment phase comprises a plurality of treatment cycles of iterations;

the ultrasound imaging unit is further configured to, before the treatment in the first treatment cycle of each treatment phase, emit imaging ultrasound waves to the imaging region and receive corresponding echoes, and based on these echoes, form a corresponding B-mode image, and obtain a vascular blood flow image based on the B-mode image; and, the region planning and parameter adjustment unit is further configured to delineate the corresponding initial lesion region and set the initial treatment parameters for the focused ultrasound unit based on the vascular blood flow image.

Optionally, the system further comprises an image fusion unit;

the ultrasound imaging unit, before the treatment in the first treatment cycle of each treatment phase, emits imaging ultrasound waves to the imaging region and receives corresponding echoes, and based on these echoes, forms a corresponding B-mode image, and obtains a vascular blood flow image, the image fusion unit registers and fuses this vascular blood flow image with a registration reference image from the image input unit to obtain a registered and fused image, the region planning and parameter adjustment unit delineates the corresponding initial lesion region and sets the initial treatment parameters for the focused ultrasound unit based on the registered and fused image.

Optionally, the registration reference image is one or more of the following:

a B-mode image, a computed tomography (CT) image, a positron emission tomography (PET) image, a magnetic resonance imaging (MRI) image, an X-ray CT image, an MRI image with contrast agents, and a vascular image obtained from X-ray CT scans with contrast agents or MRI with contrast agents.

Optionally, the treatment parameters comprises the focal length, focal intensity, focal spot size, emission frequency, emission power, duty cycle, and treatment duration of the focused ultrasound.

The embodiments of this invention can be used for hemodynamic and functional analysis of the treatment region, providing new methods for studying the microvascular blood flow changes and treatment effects of high-intensity focused ultrasound (HIFU) in the treatment of various lesions, including at least the following advantages:

(1) During the implementation of high-intensity focused ultrasound treatment, the ultrasound imaging unit and the focused ultrasound unit operate in an alternating sequence. By real-time monitoring of changes in vascular blood flow in the lesion region and calculating the lesion state based on the changes in vascular blood flow, such as determining the corresponding vascular blood flow network contour and the respective vascular density index, blood flow velocity index, blood flow volume index, blood flow direction index based on the vascular blood flow image, and re-delineating the lesion region based on the vascular blood flow network contour as well as scoring the lesion state of the re-delineated lesion region based on one or more of the vascular density index, blood flow velocity index, and blood flow volume index, comparing the scoring result with the expected result, and readjusting the treatment parameters of the focused ultrasound unit based on the comparison result for the next treatment of the re-delineated lesion region. This achieves dynamic monitoring of the entire process of changes in the lesion region, adaptively adjusting the treatment parameters of focused ultrasound based on real-time monitoring results of the lesion state until the treatment effect of the lesion region reaches the expected outcome, which can avoid damage to normal tissue caused by excessive irradiation, unnecessary energy accumulation in the body, or insufficient irradiation intensity affecting the treatment effect, realizing dynamic and precise treatment of the lesion under the mutual coordination of the focused ultrasound unit and the ultrasound imaging unit. Additionally, specific methods for obtaining blood flow velocity index, blood flow volume index, blood flow direction, and vascular density index are proposed, quantifying the scoring and changes in lesion conditions to improve the accuracy of treatment.

(2) Under conditions with or without injection of ultrasound contrast agents into the vessels, high-frame-rate, high signal-to-noise ratio quality imaging, and super-resolution ultrasound imaging of the microvasculature in the treatment region are possible. By obtaining continuous multiple frames of ultrasound images and separating clutter signals, dynamic changes in vascular blood flow are generated, allowing for more precise and clear presentation of microvascular blood flow changes under high-intensity focused ultrasound treatment, and real-time imaging from 100 frames per second to tens of thousands of frames per second can be achieved. It is also possible to perform B-mode imaging and color Doppler multimodal ultrasound imaging according to treatment needs, fuse and register MRI, PET, CT images with ultrasound images, combining the advantages of ultrafast ultrasound imaging and HIFU technology to improve imaging effects. Compared to MRI, PET, CT, etc., the embodiments of this invention have the advantages of faster imaging speed, portable equipment, lower cost, and no ionizing radiation.

(3) The ultrafast ultrasound imaging method based on multi-angle acoustic wave compound imaging can significantly improve the time and spatial resolution of imaging, holding great potential in real-time monitoring of high-intensity focused ultrasound treatment effects.

This specification contains numerous technical features distributed among various technical solutions. Listing all possible combinations of these technical features (i.e., technical solutions) would make the specification too lengthy. To avoid this problem, the technical features disclosed in the above-mentioned invention content, the technical features disclosed in various embodiments and examples in the following text, and the technical features disclosed in the drawings can all be freely combined to form various new technical solutions (which should be considered as already disclosed in this specification), unless such combinations of technical features are technically infeasible. For example, if feature A+B+C is disclosed in one example and feature A+B+D+E is disclosed in another example, and features C and D are equivalent technical means that serve the same purpose, only one of them can be chosen for technical reasons and cannot be used simultaneously. Feature E can be combined with feature C from a technical perspective. Therefore, the A+B+C+D solution should not be considered as already disclosed because it is technically infeasible, while the A+B+C+E solution should be considered as already disclosed.

DETAILED DESCRIPTION

The various aspects and examples of the present invention will now be described. The following description provides specific details for understanding and implementing these examples. However, those skilled in the art will understand that the present invention can be practiced without many of these details.

Explanation of Some Concepts in the Embodiments

Ultrasonic Tracer: Small-sized scatterers that can travel in the blood flow within vessels, producing scattering echo signals under ultrasound. Examples include: inherent red blood cells in the vessels; other cells that can be injected into the vessels, such as yeast cells or various cells edited by genetic engineering; and biocompatible artificial materials, such as ultrasound microbubble contrast agents, hydrogen peroxide bubbles, nanodroplets, etc.

Point spread function: The sound field distribution formed by a single scatterer (e.g., ultrasonic tracer) in the sound field after image reconstruction is known as the point spread function, also referred to as point expansion function.

Focal length: The distance from the focus to the center point of the ultrasound probe's emitting array elements.

Ultrasound probe: Also known as an ultrasound transducer array or ultrasound probe array, these terms refer to the same concept differently. Specifically, it is a device that adopts one or more ultrasound array elements and a digital control unit with adjustable time delay to realize the imaging or focusing treatment of the region of interest in tissue. This device possesses at least the capability to emit and collect ultrasound signals.

Focal intensity: The intensity of the sound field in the focal area.

Focal spot size: Also referred to as the lateral and longitudinal size of the focal zone, it describes the parameters of the HIFU focal area, generally focusing on a region known as the focal spot.

Duty cycle: In a pulse cycle, the proportion of the system's power-on time relative to the total time.

Image registration: Also known as displacement correction. During the imaging process, due to the relative movement between the probe and the object, especially in in vivo experiments, image displacement caused by factors such as breathing and heartbeat can affect image quality. Therefore, image registration or displacement correction is necessary to compensate for the relative movement between the probe and the object, thereby obtaining clear imaging results.

In order to make objects, technical solutions and advantages of the present invention clearer, embodiments of the present invention will be further described below in detail with reference to the accompanying drawings.

Figure 1:
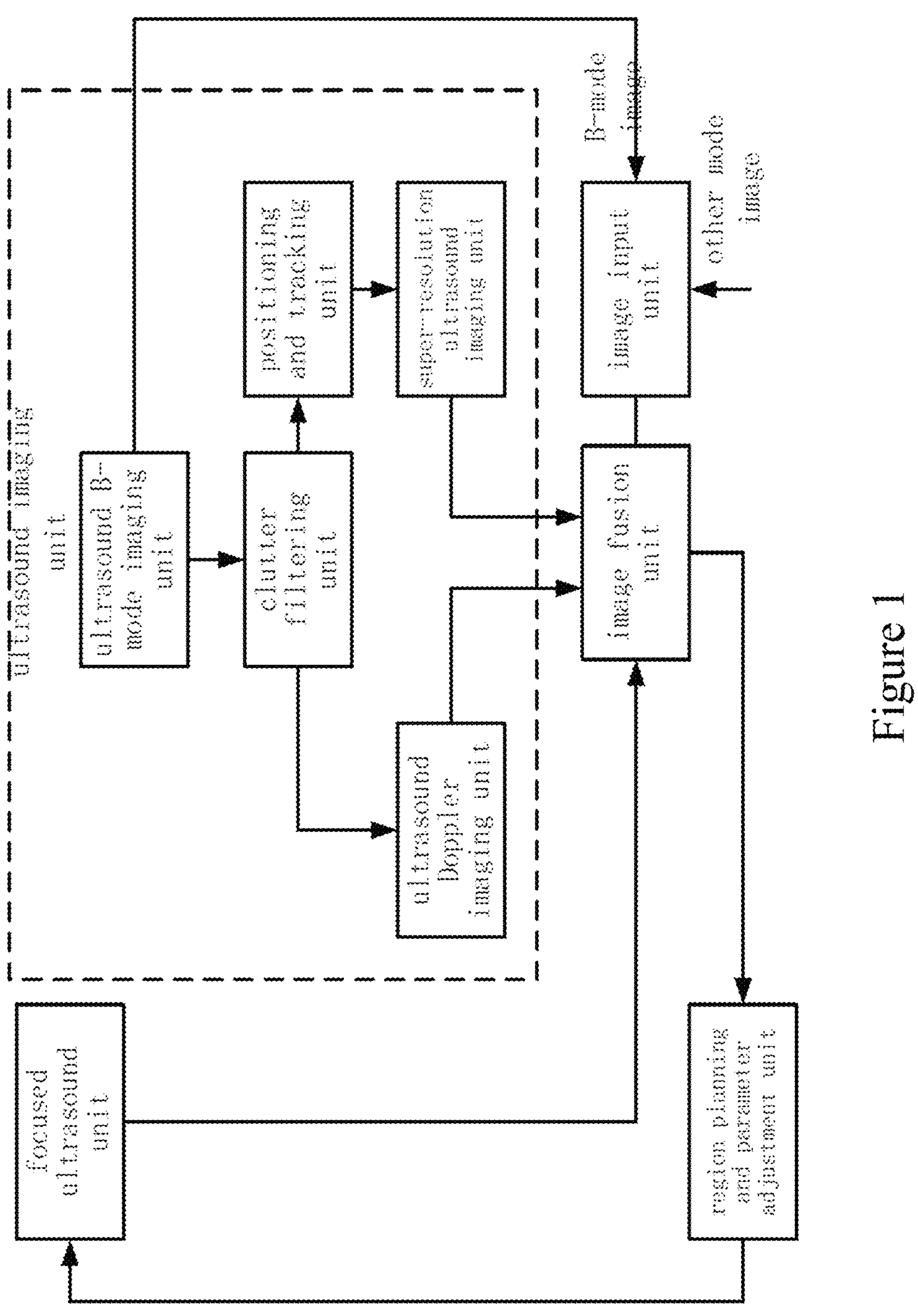
FIG. 1 is a schematic diagram of the structure of a focused ultrasound treatment system based on ultrasound imaging according to an embodiment of the present invention.

The first embodiment of the invention relates to a focused ultrasound treatment system based on ultrasound imaging, whose schematic structure is shown in FIG. 1. This system includes a focused ultrasound unit, an ultrasound imaging unit, and a region planning and parameter adjustment unit. Specifically:

The focused ultrasound unit is configured to emit focused ultrasound waves to the lesion region for treatment. Specifically, the focused ultrasound unit focuses one or more array elements through spatial or temporal delay processing, thereby being configured to emit focused ultrasound waves to the lesion region to achieve localized sound energy enhancement for treatment.

Optionally, when the focused ultrasound unit emits focused ultrasound waves to the lesion region for treatment, it can treat the lesion region in an automated planning manner or treat the lesion region in a pre-agreed (manual) manner.

The ultrasound imaging unit is configured to, after the said treatment, emit imaging ultrasound waves to the imaging region and receive corresponding echoes, and based on these echoes, form a corresponding vascular blood flow image. Specifically, the ultrasound imaging unit includes a B-mode imaging unit, which is configured to, after treatment by the focused ultrasound unit, emit imaging ultrasound waves to the imaging region and receive corresponding echoes, and based on these echoes, form a corresponding B-mode image, and the ultrasound imaging unit forms the vascular blood flow image based on this B-mode image. Preferably, the B-mode imaging unit emits a set of plane waves or curved acoustic waves at multiple deflection angles to the imaging region.

Figure 10:
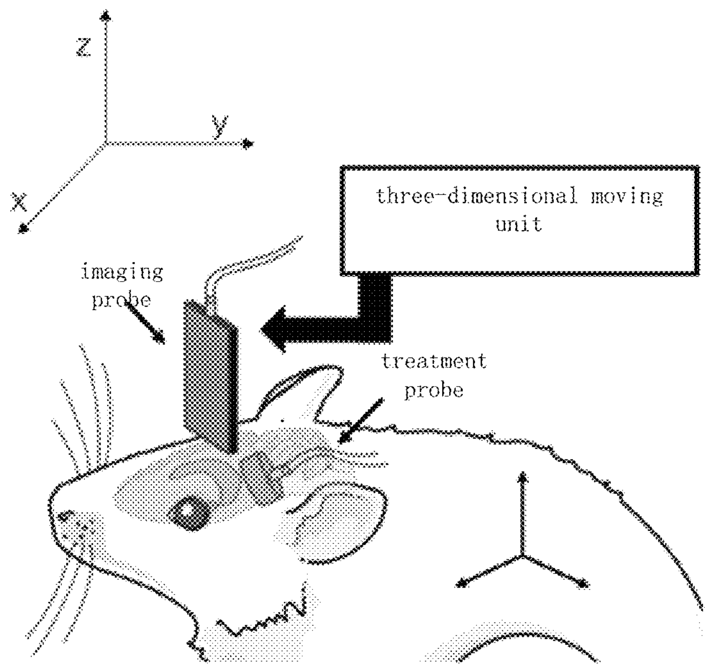
FIG. 10 is a schematic diagram of three-dimensional imaging construction in an example for treating brain lesions in rats.
Figures 31A, 31B:
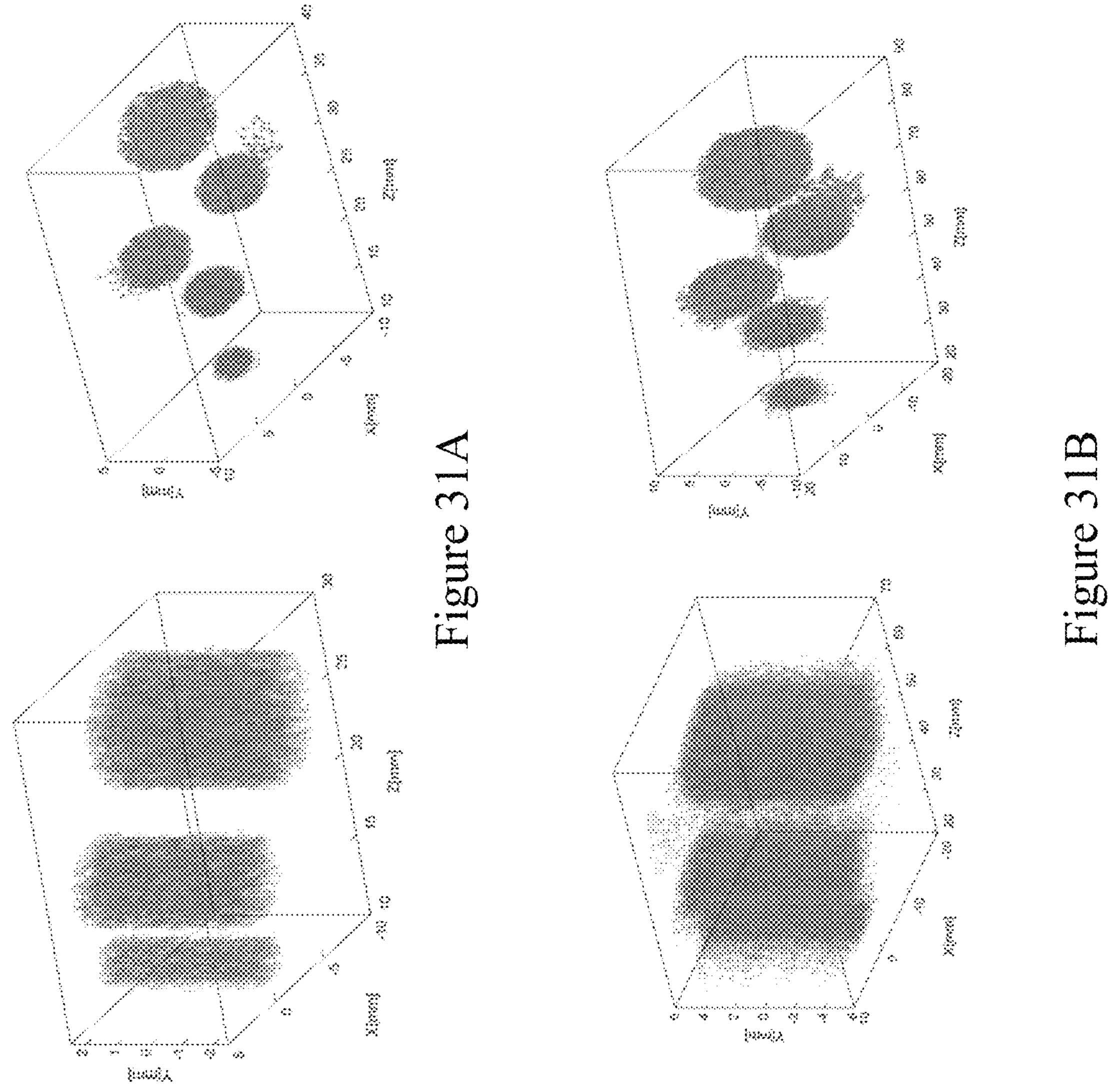
FIG. 31A is a three-dimensional tissue imaging result obtained by a three-dimensional probe with a center frequency of 6.25 MHz.
FIG. 31B is a three-dimensional tissue imaging result obtained by a three-dimensional probe with a center frequency of 3 MHz.

Optionally, the vascular blood flow image in this invention can be in two-dimensional or three-dimensional formats, among others. The implementation for the three-dimensional image of the vascular blood flow, for example, includes: as shown in FIG. 10, the system also comprises a three-dimensional moving unit, which is configured to hold and control the imaging probe of the ultrasound imaging unit to move in three-dimensional space to obtain three-dimensional images of vascular blood flow. The method for implementing the real-time scanning three-dimensional image of vascular blood flow, for example, includes: as shown in FIGS. 31A and 31B, the system further includes a two-dimensional ultrasound array element for real-time three-dimensional imaging; this two-dimensional ultrasound array element is configured to control the delay of each array element and ultrafast reception of echoes to achieve three-dimensional imaging.

Optionally, the vascular blood flow image may be microvascular blood flow image. In one embodiment, the B-mode imaging unit emits ultrasound waves at a frame rate of ≥200 frames/s, with an imaging frame rate of ≥50 frames/s, and through the imaging schematic shown in FIG. 1, the resolution of microvascular blood flow imaging is ≤the wavelength of the emitted ultrasound waves. In another embodiment, the B-mode imaging unit emits ultrasound waves at a frame rate of ≥200 frames/s, with an imaging frame rate of ≥50 frames/s, and through the imaging schematic shown in FIG. 1, the vascular blood flow image may be a super-resolution microvascular blood flow image, with a microvascular blood flow imaging resolution of ≥1/50 of the wavelength of the emitted ultrasound waves.

There are various implementations of obtaining a vascular blood flow image (for example, a microvascular blood flow image) based on the B-mode image. In one embodiment, the ultrasound imaging unit further includes a clutter filtering unit, a positioning and tracking unit, and a super-resolution ultrasound imaging unit. The clutter filtering unit performs clutter filtering on the B-mode image, the positioning and tracking unit locates and tracks red blood cells or tracers in the filtered image, and the super-resolution ultrasound imaging unit reconstructs the vascular blood flow image in the B-mode image based on the positioning and tracking results to obtain the corresponding super-resolution vascular blood flow image. Here, the tracer is introduced into the bloodstream via venous injection after each treatment. In another embodiment, the ultrasound imaging unit includes a clutter filtering unit and an ultrasound Doppler imaging unit. The clutter filtering unit performs clutter filtering on the B-mode image, and the ultrasound Doppler imaging unit performs orthogonal demodulation and frequency shift analysis on the filtered B-mode image to obtain the corresponding power Doppler vascular blood flow image or color Doppler vascular blood flow image.

The super-resolution ultrasound imaging unit uses ultrasound tracers moving in the vessels as strong scattering sources, detecting the point spread function of individual tracers from the ultrafast ultrasound collected B-mode images. The center position of its point spread function is used as the localization point of the tracer. The positions of tracers in each frame image are paired and connected to determine the trajectory of each tracer's movement. The length of the tracer's trajectory divided by the time taken for the tracer to move along the trajectory yields the blood flow velocity in the vessels traversed by the ultrasound tracer. By accumulating the trajectories of tracers' movements from thousands to millions of frame images, a super-resolution image of the vascular structure can be reconstructed. This super-resolution refers to the localization accuracy obtained by center positioning of the tracer's point spread function, which is far superior to the wavelength of the emitted sound wave. Blood flow density images based on the number and density of tracers or red blood cells, blood flow density images distinguishing upstream and downstream blood flow, and blood flow velocity images can be generated. For the blood flow density images based on the number and density of tracers or red blood cells, the intensity value of each pixel in the image depends on the number of tracers or red blood cells passing through that pixel, representing blood flow volume. In the blood flow density images distinguishing upstream and downstream blood flow, the intensity value of each pixel depends on the number of tracers or red blood cells moving up or down through that pixel, with upward or downward movement distinguished by two different colors. In the blood flow velocity image, the intensity value of each pixel depends on the average speed of the tracers or red blood cells passing through that pixel, with the average speed representing the blood flow velocity.

The region planning and parameter adjustment unit is configured to re-delineate the lesion region based on the vascular blood flow image (two-dimensional or three-dimensional, etc.) and to readjust the treatment parameters of the focused ultrasound unit for the next treatment of the re-delineated lesion region, where the imaging region includes the lesion region. Optionally, the treatment parameters may include, but are not limited to, probe parameters of the focused ultrasound unit, such as focal length, focal intensity, focal spot size, emission frequency, emission power, duty cycle, and treatment duration, either individually or in combination.

Optionally, the region planning and parameter adjustment unit is also configured to determine the corresponding vascular blood flow network contour and the respective vascular density index, blood flow velocity index, and blood flow volume index based on the vascular blood flow image (two-dimensional or three-dimensional, etc.). It re-delineates the lesion region based on the vascular blood flow network contour and scores the lesion state of the re-delineated lesion region based on one or more of the vascular density index, blood flow velocity index, and blood flow volume index. The scoring results are compared with the expected results, and based on this comparison, the treatment parameters of the focused ultrasound unit are readjusted for the next treatment of the re-delineated lesion region.

Optionally, the region planning and parameter adjustment unit is further configured to determine the vascular blood flow network contour and the direction of blood flow within the re-delineated lesion region based on the vascular blood flow image (two-dimensional or three-dimensional, etc.). It plans the treatment route based on the vascular blood flow network contour and the blood flow direction for the next treatment of the re-delineated lesion region by the focused ultrasound unit.

Optionally, the system also includes an image input unit and an image fusion unit. The image input unit is configured to output registration reference images to the image fusion unit, which is configured to register and fuse the vascular blood flow image (two-dimensional or three-dimensional, etc.) with the registration reference image to obtain a registered and fused image. The registration reference image may include, but is not limited to, the B-mode image obtained by the aforementioned B-mode imaging unit, or other modal images such as computed tomography (CT) images, positron emission tomography (PET) images, magnetic resonance imaging (MRI) images, X-ray CT images, MRI images with contrast agents, and vascular images obtained from X-ray CT scans with contrast agents or MRI with contrast agents.

Optionally, the region planning and parameter adjustment unit can also be configured to: determine the corresponding vascular blood flow network contour and the respective vascular density index, blood flow velocity index, and blood flow volume index based on the registered and fused image, and re-delineate the lesion region based on the vascular blood flow network contour as well as score the lesion state of the re-delineated lesion region based on one or more of the vascular density index, blood flow velocity index, and blood flow volume index, compare the scoring result with the expected result, and readjust the treatment parameters of the focused ultrasound unit based on this comparison for the next treatment of the re-delineated lesion region.

Optionally, the region planning and parameter adjustment unit is also configured to perform binarization processing on the vascular blood flow image to obtain the vascular blood flow network contour.

Wherein, the aforementioned "score the lesion state of the re-delineated lesion region based on one or more of the vascular density index, blood flow velocity index, and blood flow volume index" can involve scoring based on all indicators for the lesion state of the re-delineated lesion region, or it can be based on partial indicators (for example, only the vascular density index and blood flow volume index). In one embodiment, the scoring may be, but is not limited to, pre-setting scores according to the magnitude of each indicator and assigning corresponding weights to each indicator, with the score of the lesion state of the re-delineated lesion region being equal to the weighted sum of these indicators. There are various implementations of scoring the lesion state of the re-delineated lesion region based on one or more of the vascular density index, blood flow velocity index, and blood flow volume index. For example, one could calculate the sum of scores for each indicator separately to obtain the scoring result. Alternatively, a weighted sum of the vascular density index, blood flow velocity index, and blood flow volume index could be calculated to obtain the scoring result. These two examples of scoring methods are not exhaustive, and any scoring results calculated based on the vascular density index, blood flow velocity index, and blood flow volume index are within the scope of protection of this invention.

It should be noted that the aforementioned vascular density index refers to the proportion of the vascular region or volume within a unit space, i.e., vascular region or volume/space region or volume; the blood flow velocity index refers to the average blood flow velocity in the delineated lesion region; the blood flow volume index refers to the average blood flow volume in the delineated lesion region. Optionally, the methods for obtaining the vascular density index, blood flow velocity index, and blood flow volume index are as follows ①②③: ① The region planning and parameter adjustment unit, based on the super-resolution vascular blood flow image, calculates the blood flow velocity index from the quotient of the tracer trajectory length and the time taken for the tracer to move along the trajectory, or directly obtains the blood flow velocity index from power Doppler vascular blood flow images or color Doppler vascular blood flow images. ② The region planning and parameter adjustment unit, based on the vascular blood flow network contour, determines the central position points S(x,y) of each vascular blood flow within the vascular blood flow network contour and obtains the vascular blood flow radius r(x,y) at each central position point S(x,y), calculating the blood flow volume index using the formula $Q=\Sigma_{S(x,y)}v(x, y)*\pi r(x, y)^2$. Further, treatment quantification of this region can be seen by comparing changes in total blood flow volume V at various stages of treatment. If the total blood flow volume of the selected region before treatment is $V_0$, the ratio of V to $V_0$ during treatment can be used to normatively evaluate the degree of treatment, thus completing dynamic treatment planning and the treatment process. If $V/V_0=0$, it indicates that all blood flow in the selected region is zero, determined as no further treatment needed, scored as a; if $V/V_0=1$, it indicates that the blood flow volume in the selected region is the same as before treatment, i.e., effective treatment has not been formed, scored as c; if $V/V_0$ value is between 0 and 1, scored as b, a<b<c. For example, $V/V_0$ values can be further divided into several different scoring intervals. ③ The region planning and parameter adjustment unit calculates the vascular density index by the ratio of the vascular blood flow image region formed by the vascular blood flow network contour to the current imaging image area, or the ratio of the vascular blood flow image volume formed by the vascular blood flow network contour to the current imaging space volume. Further, based on a given threshold for ultrasound Doppler images or super-resolution ultrasound localization microvascular images, such as greater than 0.1 is determined as vascular area, less than 0.1 is determined as non-vascular area, thus binary processing can be applied to the images with and without blood flow, marking areas with blood flow as 1, and areas without blood flow as 0. By calculating the ratio of the number of 1s in the relevant region to the total number of pixels in the image, the vascular density ρ of that region can be obtained. ρ values range from 0 to 1, with 1 indicating the entire region is vascular, and 0 indicating no vessels in the area. By comparing the changes in the total average blood flow density ρ at different treatment stages, the quantification of treatment in that region can be understood. If the total average density ρ of the selected region before treatment is $\rho_0$, the ratio of ρ to $\rho_0$ during treatment can be used to normatively evaluate the degree of treatment, thus completing dynamic treatment planning and the treatment process. If $\rho/\rho_0=0$, it indicates that all blood flow in the selected region is zero, determined as no further treatment needed, scored as x; if $\rho/\rho_0=1$, it indicates that the blood flow density in the selected region is the same as before treatment, i.e., effective treatment has not been formed, scored as z; if $\rho/\rho_0$ value is between 0 and 1, scored as y, x<y<z. For example, $\rho/\rho_0$ values can be further divided into several different scoring intervals.

Optionally, the region planning and parameter adjustment unit can also be configured to determine the vascular blood flow network contour and the blood flow direction within the re-delineated lesion region based on the registered and fused image. It plans the treatment route based on the vascular blood flow network contour and the blood flow direction for the next treatment of the re-delineated lesion region by the focused ultrasound unit.

Optionally, the system may also include a display unit for showing the vascular blood flow images (two-dimensional or three-dimensional, etc.) outputted by the ultrasound imaging unit and/or the fused images outputted by the image fusion unit. This display is for the purpose of manually adjusting the position and angle of the treatment probe and/or the imaging probe.

Figure 2:
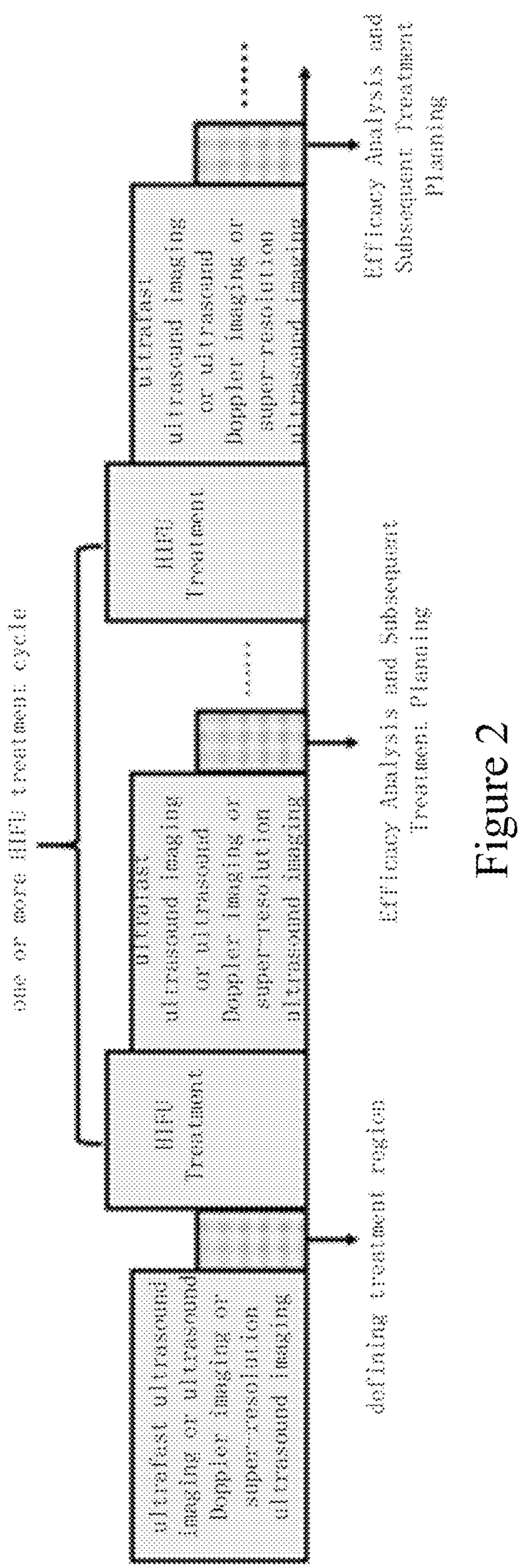
FIG. 2 is a timing diagram of the operation of the units involved in the focused ultrasound treatment system based on ultrasound imaging according to an embodiment of the present invention.

Optionally, a cycle of sequential operations of the focused ultrasound unit, the ultrasound imaging unit, and the region planning and parameter adjustment unit constitutes a treatment cycle, and each treatment phase comprises a plurality of treatment cycles of iterations, as shown in FIG. 2, where the timing only represents the relevant basic logic. In specific implementations, there are no restrictions on whether the HIFU treatment process overlaps in time with the ultrasound imaging process. Optionally, the ultrasound imaging unit is also configured to, before the treatment in the first treatment cycle of each treatment phase, emit imaging ultrasound waves to the imaging region and receive corresponding echoes, and based on these echoes, form a corresponding B-mode image, and obtain a vascular blood flow image (two-dimensional or three-dimensional, etc.) based on the B-mode image; and the region planning and parameter adjustment unit is further configured to delineate the corresponding initial lesion region and set the initial treatment parameters for the focused ultrasound unit based on the vascular blood flow image (two-dimensional or three-dimensional, etc.).

Optionally, the ultrasound imaging unit, before the treatment in the first treatment cycle of each treatment phase, emits imaging ultrasound waves to the imaging region and receives corresponding echoes, and based on these echoes, forms a corresponding B-mode image, and obtains a vascular blood flow image (two-dimensional or three-dimensional, etc.) based on the B-mode image; and the image fusion unit registers and fuses the vascular blood flow image (two-dimensional or three-dimensional, etc.) with the registration reference image; the region planning and parameter adjustment unit delineates the corresponding initial lesion region and sets the initial treatment parameters for the focused ultrasound unit based on the registered and fused image. The registration reference image may include, but is not limited to, B-mode images, computed tomography (CT) images, positron emission tomography (PET) images, magnetic resonance imaging (MRI) images, X-ray CT images, MRI images with contrast agents, and vascular images obtained from X-ray CT scans with contrast agents or MRI with contrast agents.

Figure 3:
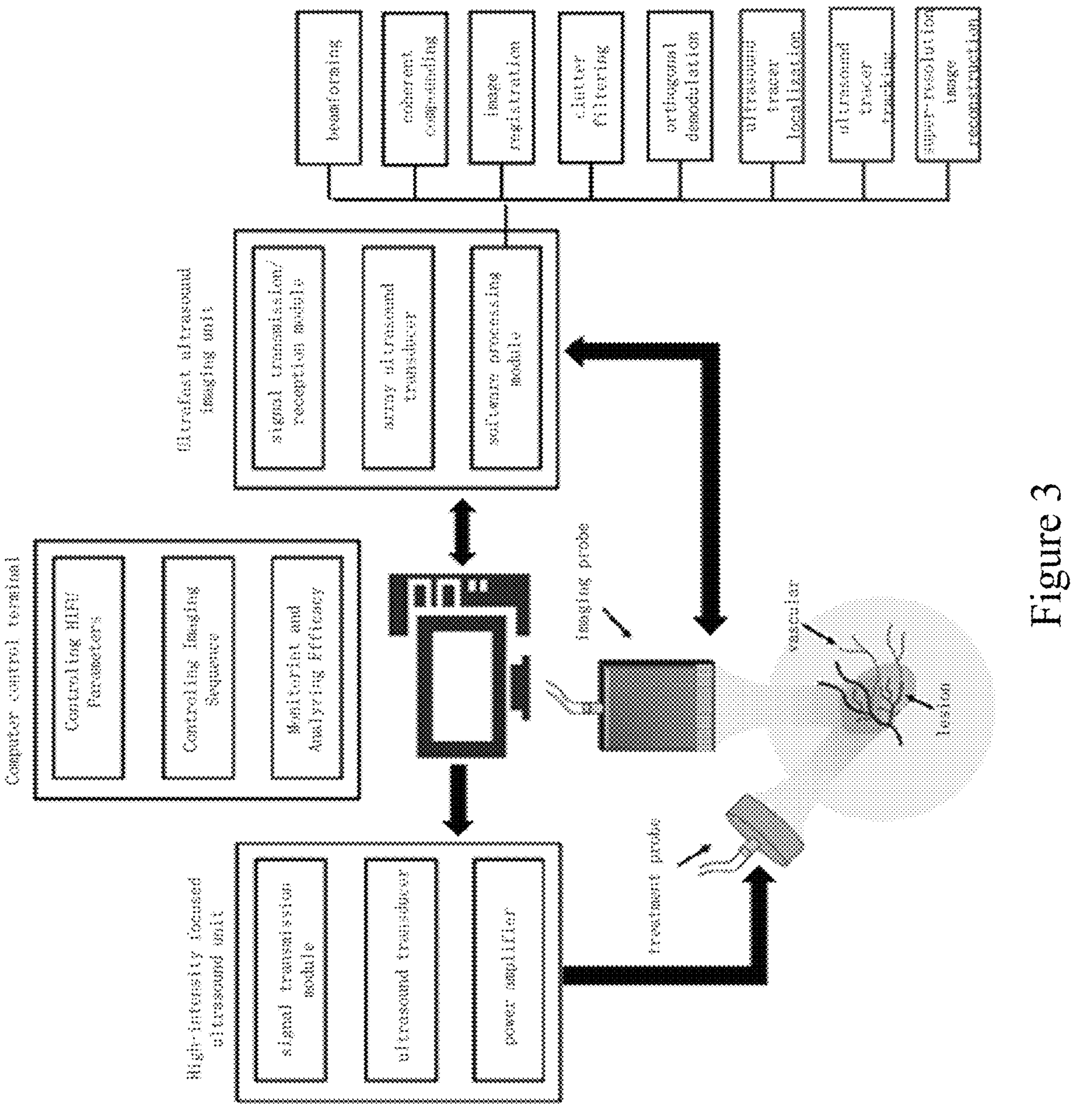
FIG. 3 is a schematic diagram of the structure of a focused ultrasound treatment system based on ultrasound imaging according to another embodiment of the present invention.

FIG. 3 shows a focused ultrasound treatment system based on vascular blood flow imaging in one embodiment. As shown in FIG. 3, it specifically includes the following parts:

a. Computer control terminal, which is an implementation of the region planning and parameter adjustment unit. The system, after each ultrasound imaging session and before high-intensity focused ultrasound (HIFU) treatment, utilizes the computer control terminal to configure the signal transmission/reception module. It adjusts parameters such as the imaging frame rate, imaging depth, and ultrasound wave deflection angle of the ultrafast ultrasound imaging unit, and excites the ultrasound transducer to emit a set of ultrasound waves at multiple deflection angles (preferably plane waves or curved sound waves) into the imaging region. This process observes the microvascular blood flow images of the treatment region (or lesion region) and surrounding normal tissue. The aforementioned ultrasound images can be registered and fused with images obtained from existing imaging methods such as MRI, PET, CT, etc., to create multimodal images, enhancing the observation of the treatment region and surrounding tissues. Based on the ultrasound images or multimodal ultrasound images, changes in blood flow in the lesion region are assessed, the treatment effect of the region is analyzed, and treatment parameters of the high-intensity focused ultrasound unit, such as ultrasound emission intensity, duration, frequency, and excitation mode, are dynamically adjusted in real-time. This adjustment changes the system's overall mechanical index (MI), thermal index (TI), spatial peak temporal average intensity (Ispta), spatial peak pulse average intensity (Isppa), and other main acoustic output indicators for appropriate treatment.

b. High-intensity focused ultrasound unit: Includes a waveform generator, power amplifier, and high-intensity focused ultrasound probe. The waveform generator can receive control signals such as trigger signals, waveform settings, sound field intensity, frequency, etc., from the computer control terminal and generate ultrasound signals in corresponding timing. The power amplifier is used to provide power output for the high-intensity focused ultrasound probe, which emits ultrasound waves into the treatment region.

c. Ultrafast ultrasound imaging unit: Compared to conventional ultrasound imaging systems that operate at hundreds of frames per second, the ultrafast ultrasound imaging unit can image from 100 frames per second to tens of thousands of frames per second. It specifically includes: a signal transmission/reception module, an array ultrasound transducer, and a software processing module. The ultrafast ultrasound imaging unit is used for sampling and storing the ultrasound radio frequency (RF) echo signals reflected or backscattered within a certain time frame from the imaging region. Optionally, the software processing module may perform beamforming, coherent compounding, image registration, clutter filtering, and orthogonal demodulation on the collected ultrasound RF echo signals to generate images and display real-time ultrafast power Doppler or ultrafast color Doppler blood flow change images of the treatment region on the monitor. Alternatively, the software processing module may also perform beamforming, coherent compounding, image registration, clutter filtering, orthogonal demodulation, ultrasound tracer localization, ultrasound tracer tracking, and super-resolution image reconstruction on the collected ultrasound RF echo signals to generate super-resolution images and display blood flow density images based on the quantity of ultrasound tracers in the treatment region, blood flow density images distinguishing upstream and downstream blood flow, and blood flow velocity images on the monitor. The signal transmission/reception module can further include a waveform generator, D/A converter, A/D converter, data storage, signal amplifier, etc.; following the current imaging sequence, after the waveform generator produces signals of specific waveforms and frequencies, these are converted to analog signals by the D/A converter, amplified by the signal amplifier, and then the ultrasound transducer is excited to emit ultrasound pulse signals, with the pulse emission interval being greater than the longest time required for the ultrasound waves to travel back and forth within the target imaging region; according to the predetermined imaging depth, amplifying, sampling, and storing the ultrasound RF echo signals a certain time after signal emission. The array ultrasound transducer can both vibrate under electrical signal excitation to generate ultrasound signals and receive ultrasound signals to convert them into electrical signals; to achieve imaging within a certain area, it often requires using multiple array elements to form an ultrasound transducer array, common types of ultrasound probes include linear arrays, convex arrays, and two-dimensional matrix arrays, but this invention does not limit the types of ultrasound transducer arrays used. The software processing module can further include beamforming module, coherent compounding module, image registration module, clutter filtering module, and orthogonal demodulation module; after collecting the ultrasound RF echo data, it is necessary to first perform beamforming to obtain an initial image, wherein beamforming algorithms include delay-and-sum algorithm, frequency domain-beam domain migration algorithm for beamforming, etc.; preferably, coherently compounding images obtained from a set of single or multiple deflection angles of plane or curved sound waves can effectively improve the signal-to-noise ratio and resolution of the image, obtaining high-quality B-mode ultrasound images; when sampling the ultrasound RF echo signals, preferably using 2×, 3×, 4×, or higher of the center frequency of the transmit signal as the sampling frequency, thus obtaining a band-pass signal (RF) carried by the center frequency, the orthogonal demodulation step filters out the carrier signal, obtaining the in-phase and quadrature components (IQ); during imaging, the probe and the object often experience certain relative displacement, especially in in vivo experiments; image displacement caused by breathing can affect image quality, thus image registration is required to compensate for the relative displacement between the probe and the object; the received echo data contains echo signals from static tissue, echo signals from blood flow, and noise; to clearly observe micro-blood flow in the image, noise and static tissue signal data are filtered out from the image data after motion calibration; current common methods include high-pass filtering, adaptive filtering, singular value decomposition, robust principal component analysis, independent component analysis, etc.

Figure 4:
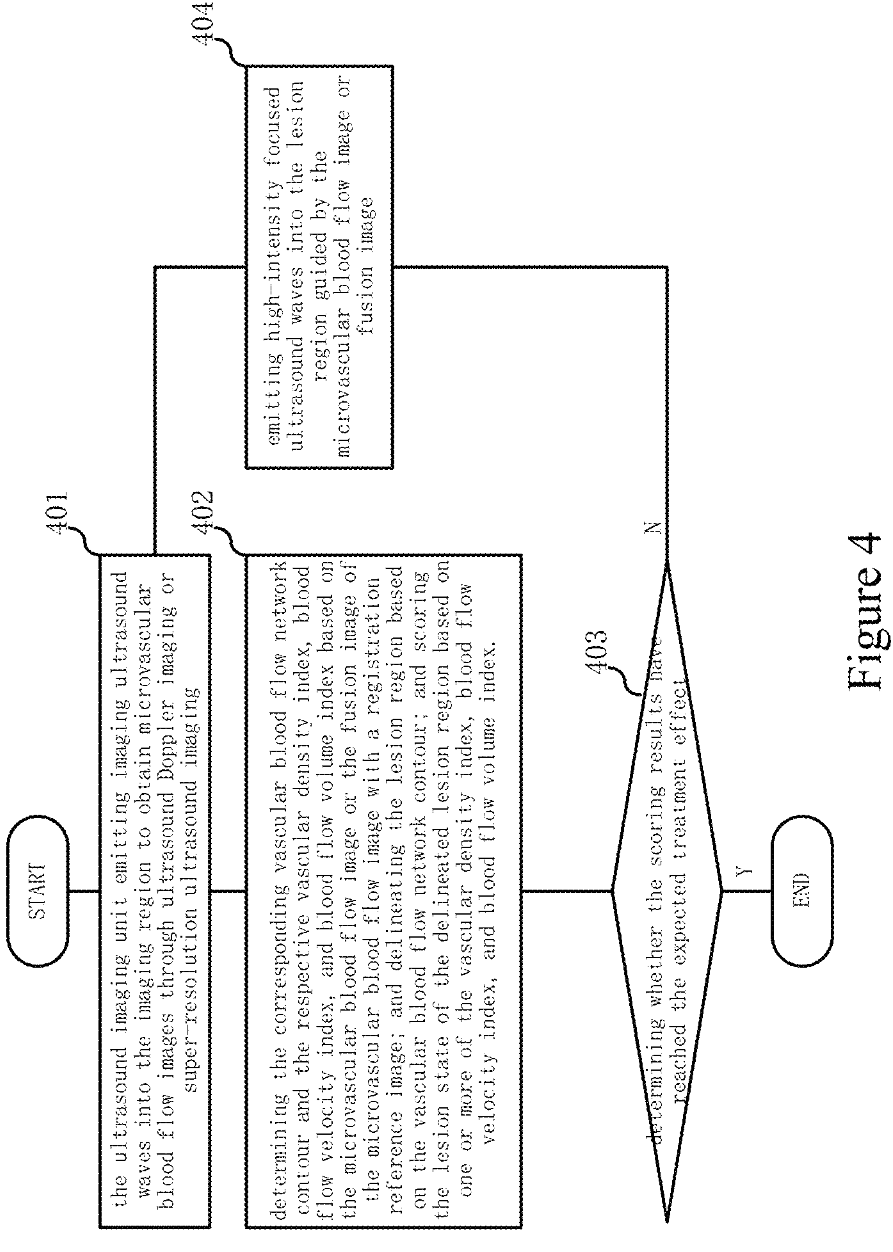
FIG. 4 is an operational process flowchart of the focused ultrasound treatment system based on ultrasound imaging in the embodiment of FIG. 3.

Operational Process:

FIG. 4 illustrates the operational flowchart of the treatment system shown in FIG. 3. The process includes the following steps: In step 401, the ultrasound imaging unit emits imaging ultrasound waves into the imaging region to obtain microvascular blood flow images through ultrasound Doppler imaging or super-resolution ultrasound imaging. Next, step 402 involves determining the corresponding vascular blood flow network contour and the respective vascular density index, blood flow velocity index, and blood flow volume index based on the microvascular blood flow image or the fusion image of the microvascular blood flow image with a registration reference image. The lesion region is delineated based on the vascular blood flow network contour, and the lesion state of the delineated lesion region is scored based on one or more of the vascular density index, blood flow velocity index, and blood flow volume index. Then, in step 403, it is determined whether the scoring results have reached the expected treatment effect; if not, then step 404 involves emitting high-intensity focused ultrasound waves into the lesion region guided by the microvascular blood flow image or fusion image; otherwise, the treatment concludes. After step 404, the process returns to step 401 until the scoring results meet the expected treatment effect.

Optionally, in step 401 of the operational process, one may manually choose between ultrasound Doppler imaging or super-resolution ultrasound imaging to obtain microvascular blood flow images as needed. For example, super-resolution ultrasound imaging can be selected for imaging and treatment during the initial treatment cycle of each treatment phase, and ultrafast ultrasound imaging or ultrasound Doppler imaging can be chosen for imaging and treatment in subsequent treatment cycles.

Optionally, in step 401 of the operational process, imaging ultrasound waves can be specifically emitted into the imaging region to obtain B-mode images, and based on the B-mode images, either super-resolution ultrasound imaging or ultrasound Doppler imaging can be chosen to obtain microvascular blood flow images. For instance, if ultrasound tracers are not injected, imaging ultrasound waves are emitted into the imaging region to obtain B-mode images, and based on the obtained B-mode images, power Doppler and color Doppler microvascular blood flow images are generated. Without injecting ultrasound tracers, after obtaining B-mode images, super-resolution microvascular blood flow images can also be generated based on the B-mode images through red blood cell positioning, tracking, and image reconstruction. If ultrasound tracers are injected, emitting imaging ultrasound waves into the imaging region to obtain B-mode images allows for the generation of super-resolution microvascular blood flow images through ultrasound tracer positioning, tracking, and image reconstruction.

Example 1

Figure 5:
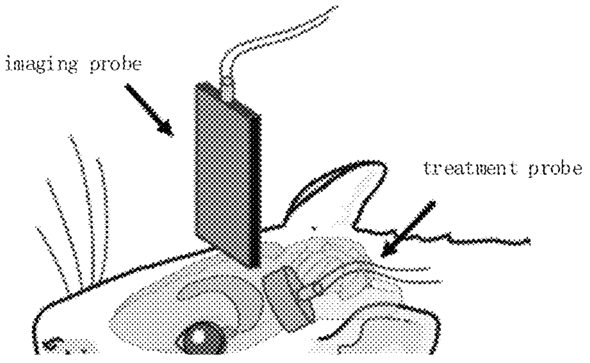
FIG. 5 is a diagram showing the placement of the ultrasound probe in an example for treating brain lesions in rats.

To better understand the technical solution of this invention, the following is an explanation combined with a specific example. This example involves using the focused ultrasound treatment system based on ultrasound imaging of the present invention to treat and image the brain blood flow of adult rats with high-intensity focused ultrasound in the treatment region and surrounding tissues. However, the invention is not limited to the treatment and imaging of rat brains. The specific operational steps are as follows:

(1) The probe of the high-intensity focused ultrasound unit and the probe of the ultrafast ultrasound imaging unit are fixed in the same vertical plane, with the ultrasound imaging probe placed directly above the rat's head and the high-intensity focused ultrasound probe placed to one side. The angle between the high-intensity focused ultrasound probe and the vertical direction can be changed as needed, as shown in FIG. 5, using medical ultrasound coupling gel for coupling. In this example, the high-intensity focused ultrasound probe used is a single-array element probe with a center frequency of 956 kHz and a focal length of 6.0 mm. In practical applications, high-intensity focused ultrasound probes with different center frequencies, focal lengths, and numbers of array elements may be freely chosen according to different requirements for treatment region size and intensity. The ultrasound probe is connected to a multi-channel ultrasound transmission and reception device.

(2) Transmission and echo data collection of multi-angle coherent plane waves. In this example, a linear array ultrasound probe with a center frequency of 15.6 MHz and 128 channels is used, transmitting plane waves at 23 different deflection angles per set. The echo signals are converted into voltage signals by the ultrasound transducer and processed by an analog signal amplifier and a filter, followed by analog-to-digital conversion and data storage, where the sampling frequency for the analog-to-digital conversion is four times the center frequency of the ultrasound signal used for imaging. If the imaging region depth is d, the total length of the probe array is L, and the speed of ultrasound in soft tissue is c, then the shortest time interval between two ultrasound plane wave transmissions is $$t = 2 * \frac{\sqrt{d^2 + L^2}}{c};$$

if the number of inclined plane waves per set is N, then the maximum frame rate is $$K = \frac{1}{N * t}.$$

In practical applications, ultrasound imaging probes with different center frequencies, focal lengths, and numbers of array elements are chosen according to different requirements for treatment region size and intensity.

(3) Beamforming. In this example, the frequency domain-beam domain migration algorithm is used for beamforming, reconstructing images from stored echo signals. Then, the 23 images reconstructed from the echo signals of each set of 23 deflection angle plane waves are coherently compounded to produce a high-quality ultrasound B-mode image. The composite imaging frame rate in this embodiment is 500 Hz, with a sampling time of 0.6s, resulting in a total of 300 compounded images. Parameters used for image reconstruction, such as imaging frame rate and sampling time, can be selected based on actual needs.

(4) Clutter filtering. In this example, singular value decomposition is used for clutter filtering. S(x, z, t) is a three-dimensional spatio-temporal matrix of size ($n_x \times n_z \times n_t$), representing the information of 300 coherently compounded images, where x=960, z=128, t=300. This three-dimensional matrix S(x, z, t) is transformed into a two-dimensional matrix form Y of size ($n_x \times n_z \times n_t$), and then singular value decomposition is performed on it as shown in equation (1):

$$Y = U * \sum * V^T \quad (1)$$

where Σ is a diagonal matrix of dimension ($n_x \times n_z$, $n_t$) with its diagonal entries being the singular values of Y. U and V are orthogonal unit matrices of dimensions ($n_x \times n_z$, $n_x \times n_z$) and ($n_t$, $n_t$) respectively, whose columns correspond to the spatial and temporal singular vectors of Y.

After decomposing the 300-frame image matrix, singular values are arranged from largest to smallest. The larger singular values correspond to tissue signals, and the smaller singular values correspond to noise signals, with intermediate singular values representing dynamic blood flow signals. Low and high threshold values ($n_1$, $n_2$) are set to extract dynamic blood flow signals, in this example, $n_1$=20, $n_2$=240. By calculating according to equation (2), clutter filtering is achieved to obtain microvascular blood flow images:

$$S_{mbrain}(x, z, t) = \sum_{i=n_1}^{i=n_2} \lambda_i * U_i(x, z) * V_i(t) \quad (2)$$

where $U_i$(x, z) and $V_i$(t) represent the column vectors in matrices U and V corresponding to the singular value $\lambda_i$ in equation (1).

Figure 6:
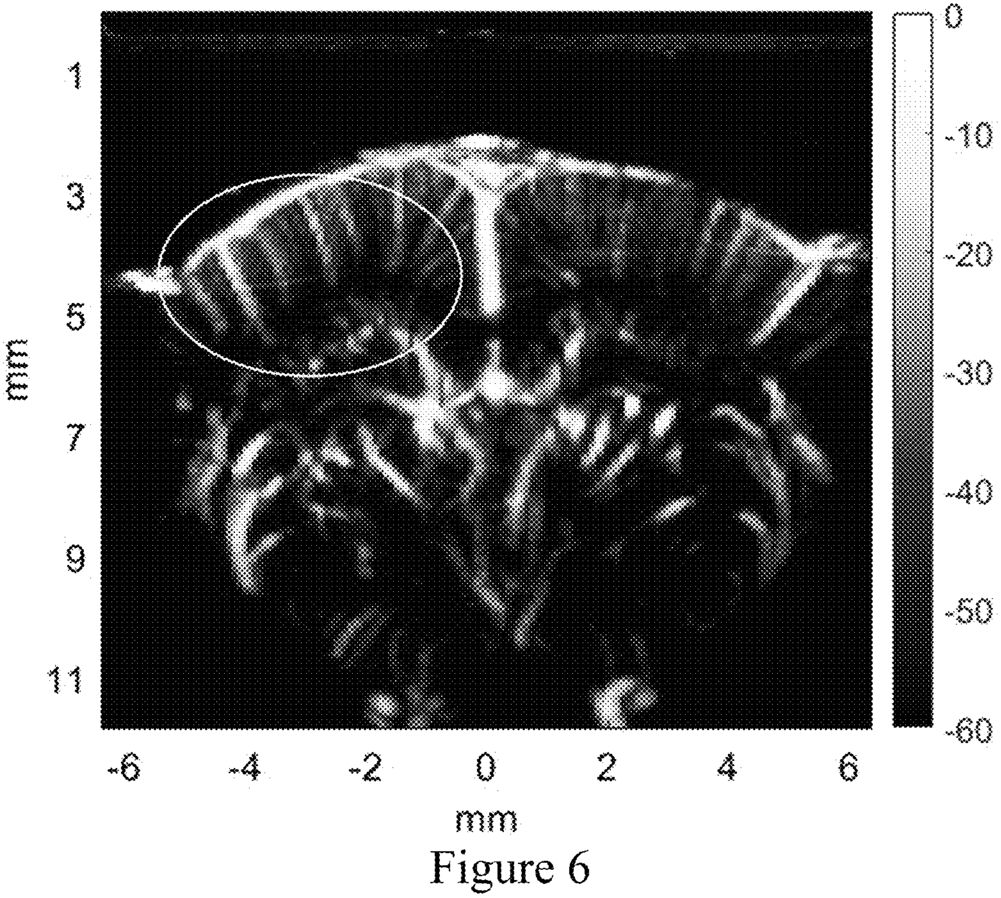
FIG. 6 is a two-dimensional image of ultrafast ultrasound power Doppler microvascular blood flow after pre-treatment clutter filtering in Example 1 for treating brain lesions in rats.
Figures 7, 8:
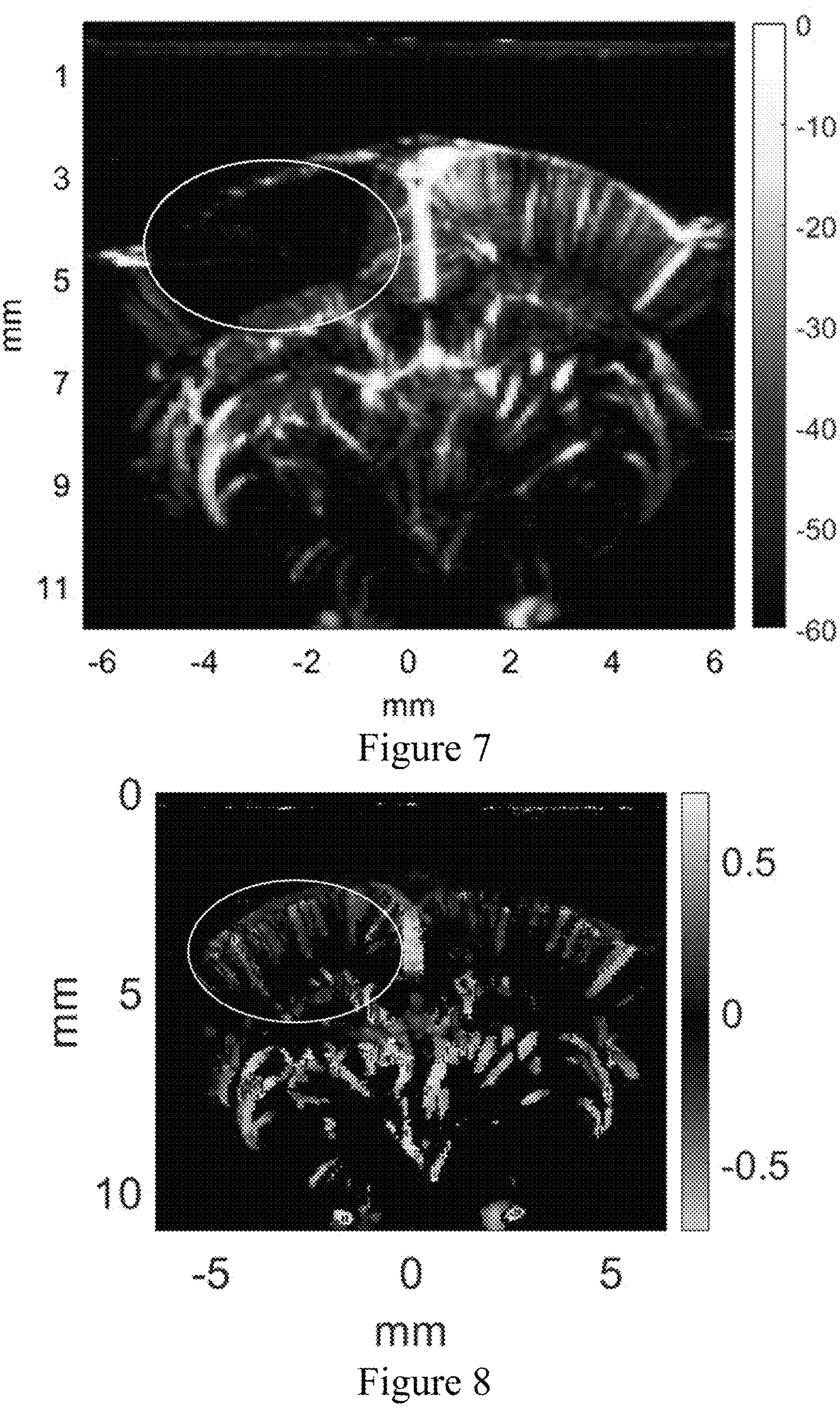
FIG. 7 is a two-dimensional image of ultrafast ultrasound power Doppler microvascular blood flow after treatment of the same region of the rat brain as in FIG. 6 in Example 1.
FIG. 8 is a two-dimensional image of ultrafast ultrasound color Doppler microvascular blood flow after pre-treatment clutter filtering in Example 1 for treating brain lesions in rats.
Figure 11:
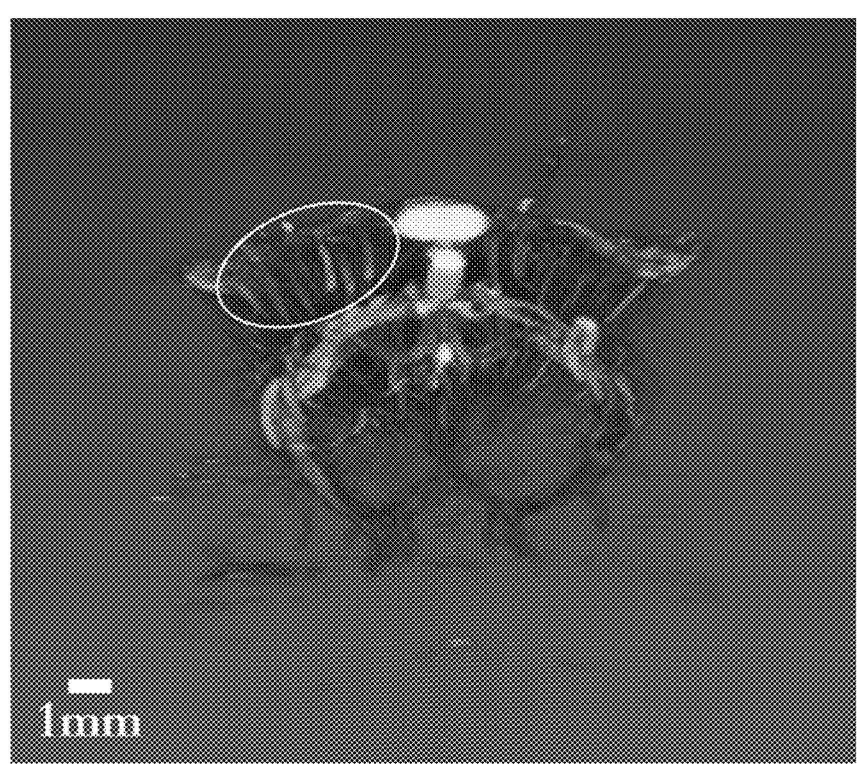
FIG. 11 is a three-dimensional image of ultrafast ultrasound power Doppler microvascular blood flow after pre-treatment clutter filtering in Example 1 for treating brain lesions in rats.

The dynamic blood flow signals extracted after clutter filtering are processed through orthogonal demodulation, frequency shift analysis, taking the modulus, taking the logarithm, and adjusting contrast to obtain the pre-treatment power Doppler 2D imaging results as shown in FIG. 6, or the pre-treatment color Doppler 2D imaging results as shown in FIG. 8. Additionally, a three-dimensional moving unit as shown in FIG. 10 is set up, through which the imaging probe is held and controlled to perform power Doppler 3D imaging of the same region of the rat brain, as shown in FIG. 11. FIGS. 6, 8, and 11 can clearly display the microvascular blood flow images of the rat brain before the high-intensity focused ultrasound treatment, with 3D imaging results being superior to 2D.

(5) Blood Flow Velocity Orthogonal demodulation

Orthogonal demodulation yields I and Q signals. The image data after clutter filtering is a band-pass signal centered at frequency $f_c$, and by multiplying this data with $e^{j2\pi f_c t}$ and then applying low-pass filtering, the orthogonally demodulated low-pass signal IQ, with real part I and imaginary part Q, is obtained:

$$IQ \stackrel{def}{=} I + iQ = Ae^{i\varphi}$$

where A and φ represent the echo strength and phase at each pixel in the image, respectively, and A can be obtained by taking the modulus of the IQ signal:

$$|IQ| = \sqrt{I^2 + Q^2} = A$$

Power Doppler Imaging (PDI) based on the B-mode images obtained from the ultrafast ultrasound imaging unit, through clutter filtering and orthogonal demodulation, yields corresponding Doppler vascular blood flow images.

$$PDI = \sum_{t=1}^{NF} IQ(x, z, t)\overline{IQ(x, z, t)}$$

where PDI represents the power Doppler blood flow image, and $\overline{IQ(x,z,t)}$ is the complex conjugate of the IQ signal.

Color Doppler imaging is based on the autocorrelation of the IQ signal for color Doppler imaging. The autocorrelation function of the IQ signal is:

$$\mathcal{R}_1 = \sum_{k=1}^{NF-1} IQ_k\overline{IQ_{k+1}} = \sum_{k=1}^{NF-1} A_k A_{k+1} e^{i(\varphi_k - \varphi_{k+1})}$$

where $\mathcal{R}_1$ is the autocorrelation matrix of the IQ signal, NF is the number of frames used for the original image, and $\overline{IQ_{k+1}}$ is the conjugate of the IQ signal for frame k+1.

Assuming $\varphi_{k+1} - \varphi_k = \Delta\varphi$, Δφ is constant for all ∀k∈[1, NF−1], then $\mathcal{R}_1$ can be represented as:

$$\mathcal{R}_1 = \underbrace{\left[\sum_{k=1}^{NF-1} A_k A_{k+1}\right]}_{\alpha} e^{-i\Delta\varphi} = \alpha e^{-i\Delta\varphi}$$

Using the logarithm rule, we get $\ln(\mathcal{R}_1) = \ln(\alpha) - i\Delta\varphi$, hence $\Delta\varphi = -\mathrm{Im}\{\ln(\mathcal{R}_1)\}$.

The Doppler velocity can be calculated from the Doppler equation $$v_D = \frac{c}{2}\frac{\Delta f}{f_c},$$

where $f_c$ is the center frequency of the transmitted ultrasound signal. The frequency shift is related to the phase shift as $\Delta\varphi = \Delta\omega\Delta\tau = 2\pi\Delta f\Delta\tau$, where Δτ is the time interval between two frames. Doppler velocity is then calculated by $$v_D = -\frac{c\,PRF}{4\pi f_c}\mathrm{Im}\{\ln(\mathcal{R}_1)\},$$

with positive Doppler velocity indicating movement towards the probe and negative away from the probe, where PRF is the pulse repetition frequency.

(6) The high-intensity focused ultrasound probe was used to destruct (or treat) the left side tissue of the rat's brain on the same plane as the ultrafast ultrasound imaging probe. A sinusoidal wave excitation was employed, with an excitation signal amplitude of 30 V, frequency of 956 kHz, and duration of 150 s. The focus was located 2 mm below the left cerebral cortex of the rat.

Figure 9:
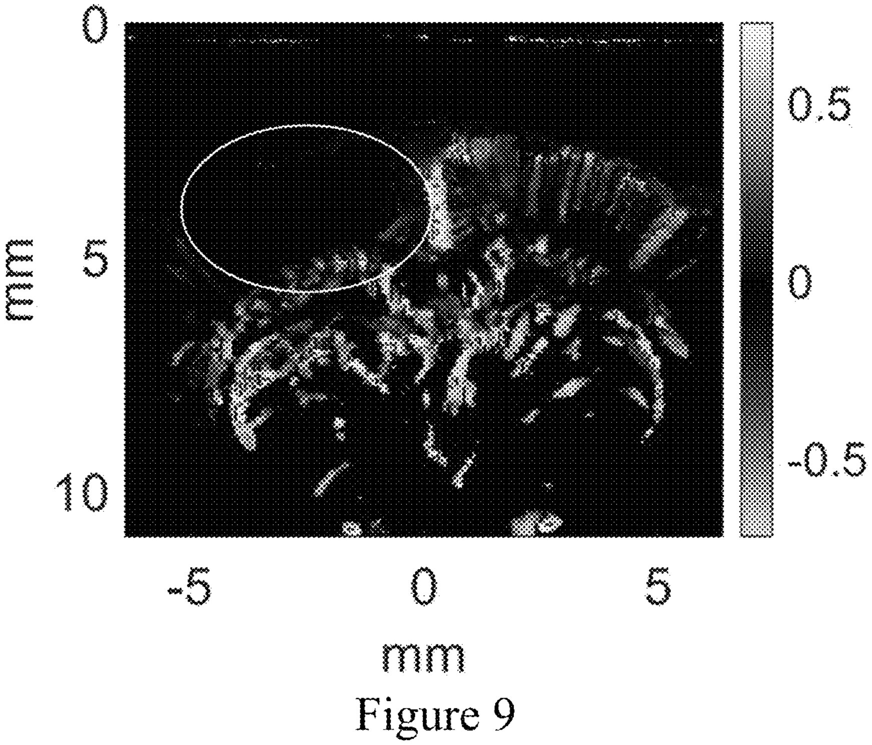
FIG. 9 is a two-dimensional image of ultrafast ultrasound color Doppler microvascular blood flow after treatment of the same region of the rat brain as in FIG. 8 in Example 1.
Figure 12:
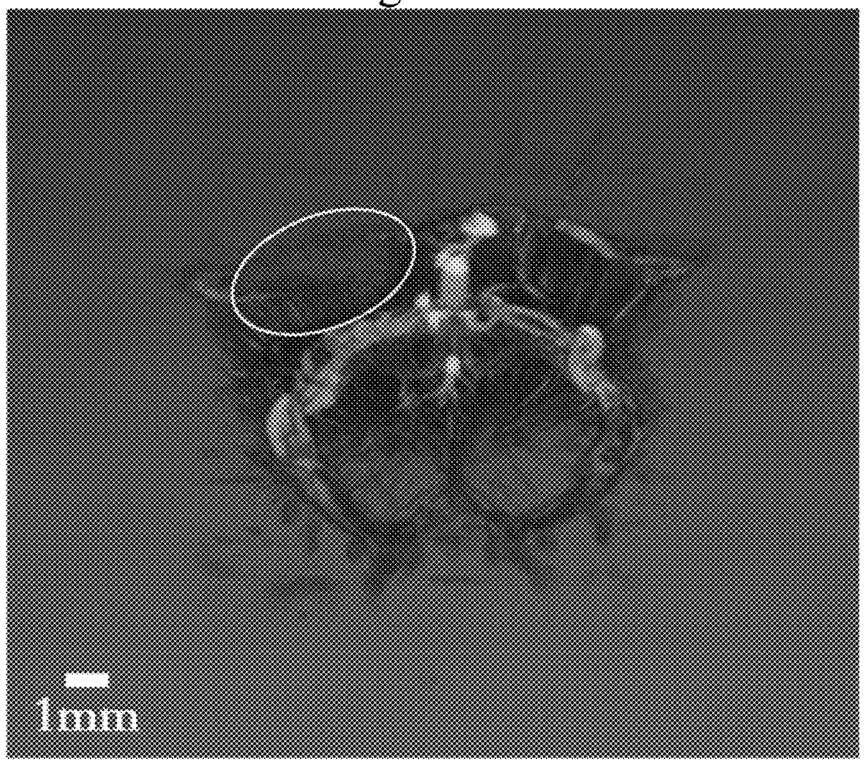
FIG. 12 is a three-dimensional image of ultrafast ultrasound power Doppler microvascular blood flow after treatment of the same region of the rat brain as in FIG. 11 in Example 1.

(7) Repeating steps (2) to (5), after one treatment session, power Doppler 2D imaging results obtained by ultrafast ultrasound imaging of the imaging region are shown in FIG. 7, color Doppler 2D imaging results are shown in FIG. 9, and power Doppler 3D imaging results are shown in FIG. 12. Based on the obtained microvascular blood flow imaging results, corresponding indices such as vascular density, blood flow volume changes, and blood flow velocity were determined to analyze the treatment effect (i.e., tissue destruction effect) in the treatment region. If the tissue destruction effect did not reach the expected outcome, the high-intensity focused ultrasound treatment parameters could be adjusted and the treatment repeated as described in (5).

Figure 13:
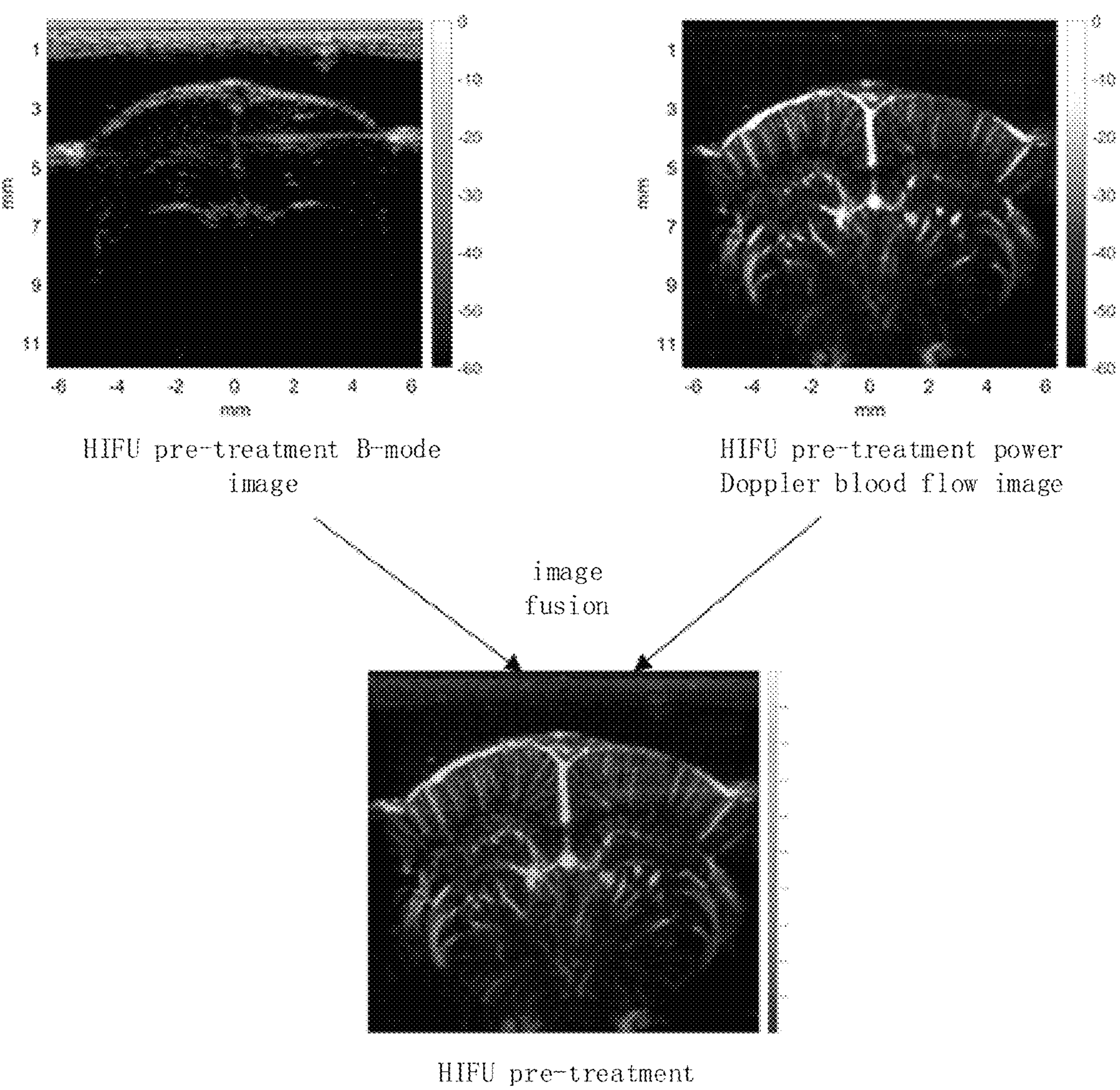
FIG. 13 is a schematic diagram of the pre-treatment fusion image A obtained by fusing the pre-treatment microvascular blood flow image with the pre-treatment B-mode image in Example 1 for treating brain lesions in rats.
Figure 14:
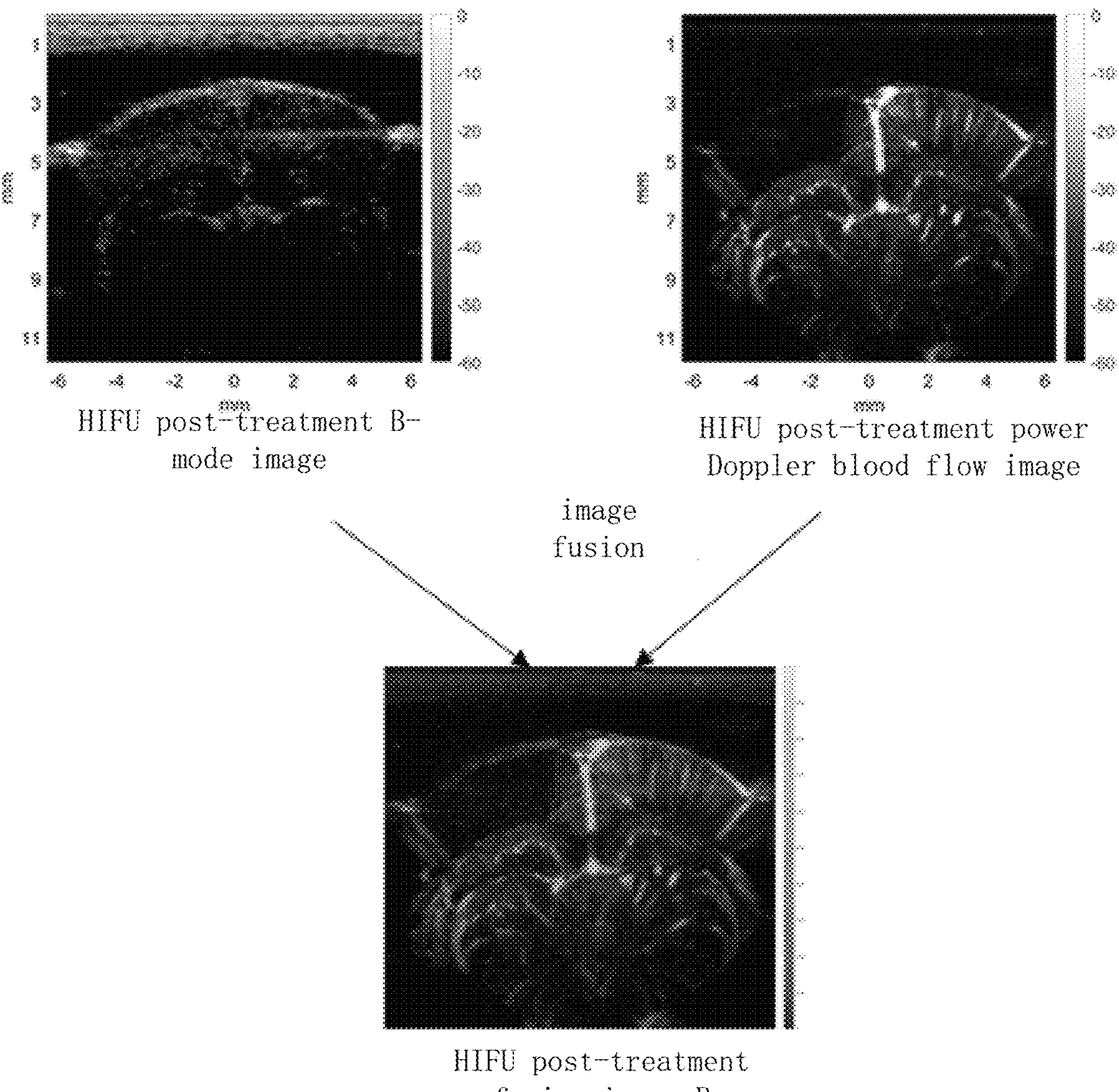
FIG. 14 is a schematic diagram of the post-treatment fusion image B obtained by fusing the post-treatment microvascular blood flow image with the post-treatment B-mode image in Example 1 for treating brain lesions in rats.
Figure 26:
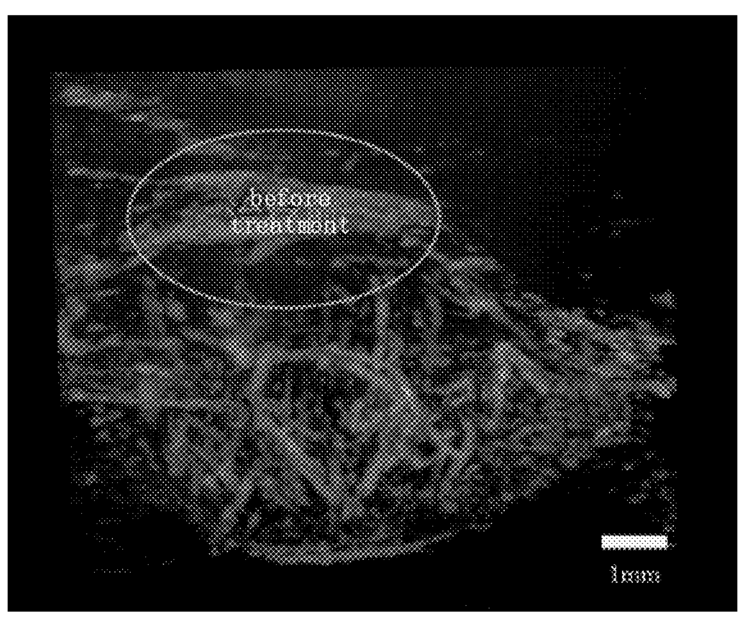
FIG. 26 is a three-dimensional image of ultrafast ultrasound power Doppler microvascular blood flow of a tumor before treatment in an example for treating melanoma in mice.
Figure 27:
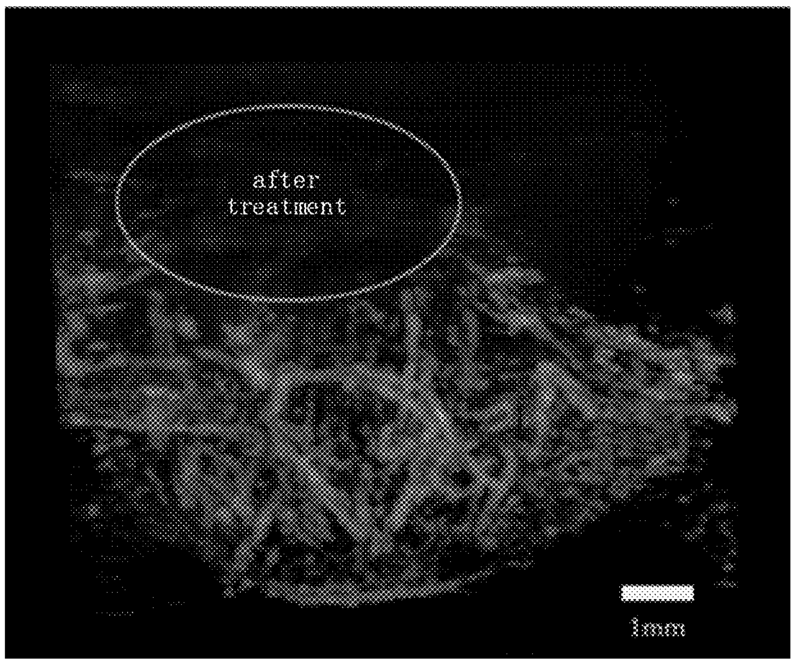
FIG. 27 is a three-dimensional image of ultrafast ultrasound power Doppler microvascular blood flow of a tumor after treatment in an example for treating melanoma in mice.
Figure 28:
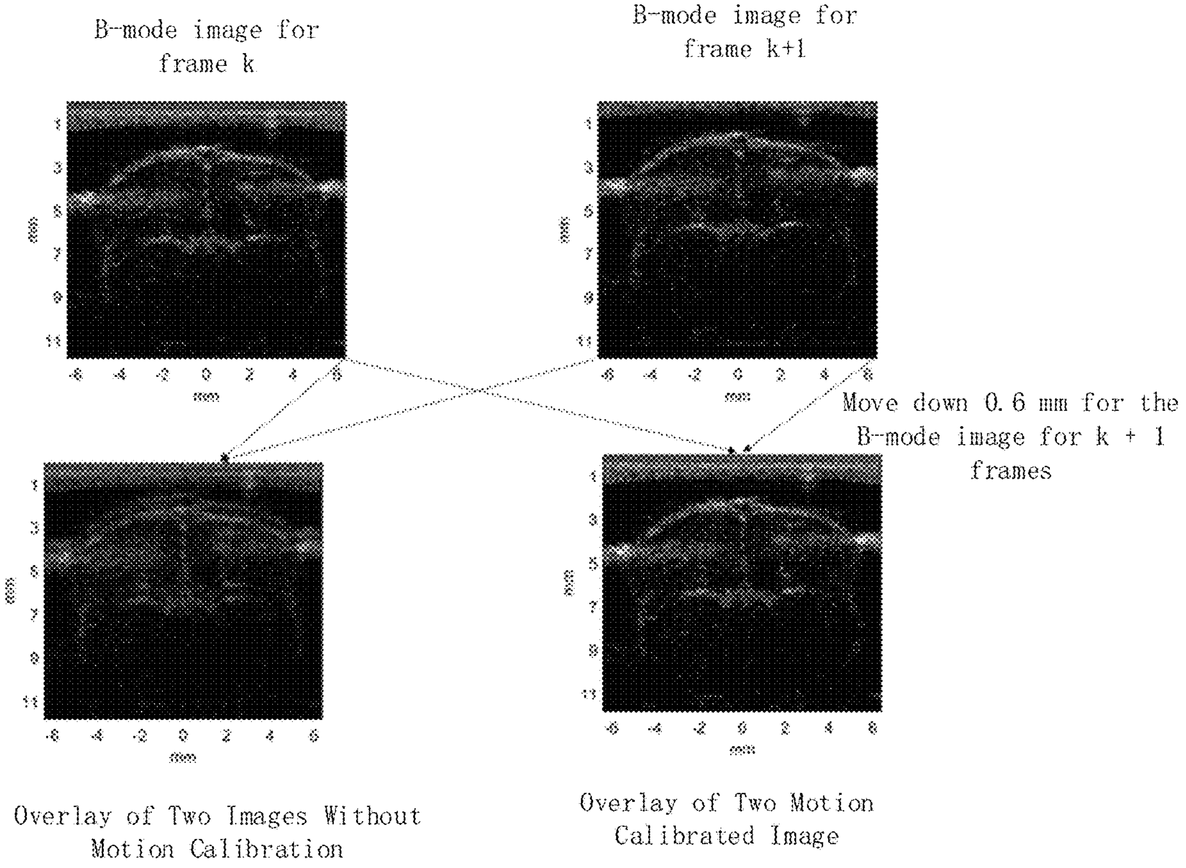
FIG. 28 is a schematic diagram illustrating a motion calibration process for example microvascular blood flow images.

From the above example, it can be known that the embodiment of the invention, during the process of lesion treatment, obtains microvascular blood flow images through the ultrafast ultrasound imaging unit. Based on these microvascular blood flow images, corresponding indices such as vascular density, blood flow volume changes, and blood flow velocity are determined. These indices are then used to calculate the treatment effect (i.e., tissue destruction effect) in the treatment region. According to the treatment effect, the treatment parameters of the focused ultrasound unit are adaptively adjusted, enabling precise treatment of the lesion through the coordinated operation of the high-intensity focused ultrasound unit and the ultrafast ultrasound imaging unit. To better demonstrate the effect of the invention, FIGS. 6 and 7 are compared, as well as FIGS. 8 and 9. It can be seen that the post-treatment microvascular blood flow images obtained by the implementation of the invention are clear and complete, allowing for the accurate determination of corresponding indices such as vascular density, blood flow volume changes, and blood flow velocity. This ensures the reliability of the calculated treatment effect and the adjusted treatment parameters, indicating the feasibility and reliability of the implementation of the invention. Furthermore, by comparing FIGS. 6, 7 with FIGS. 11, 12, it can be observed that the imaging results of 3D microvascular blood flow images are superior to 2D, enhancing the accuracy of indices such as vascular density, blood flow volume changes, and blood flow velocity, and thereby improving the accuracy of the calculated treatment effect and the adjusted treatment parameters. Furthermore, by fusing the pre-treatment microvascular blood flow image with the pre-treatment B-mode image to obtain the pre-treatment fused image A (as shown in FIG. 13), and fusing the post-treatment microvascular blood flow image with the post-treatment B-mode image to obtain the post-treatment fused image B (as shown in FIG. 14), and comparing fused images A and B, it can be seen that the fused images obtained by the implementation of the invention are clearer than the microvascular blood flow images before fusion. Therefore, the accuracy of indices such as vascular density, blood flow volume changes, and blood flow velocity can be further improved, thereby enhancing the accuracy of the calculated treatment effect and the adjusted treatment parameters. The invention is not limited to the treatment and imaging of rat brains and can also be applied to the treatment and imaging of tumors. FIGS. 26 and 27 show the pre-treatment tumor ultrafast ultrasound power Doppler microvascular blood flow 3D image and the post-treatment tumor ultrafast ultrasound power Doppler microvascular blood flow 3D image of a mouse melanoma, respectively.

Example 2

To further understand the technical solution of this invention, another specific example is provided below. This example utilizes the focused ultrasound treatment system based on ultrasound imaging of the invention to treat and image the brain blood flow in adult rats with high-intensity focused ultrasound in the treatment region and surrounding tissues. However, the invention is not limited to the treatment and imaging of rat brains. The specific operational steps are as follows:

(1) Probe Placement. The probe of the high-intensity focused ultrasound unit and the probe of the ultrafast ultrasound imaging unit are fixed in the same vertical plane. The imaging ultrasound probe is placed directly above the rat's head, and the high-intensity focused ultrasound probe is placed to one side. The angle between the high-intensity focused ultrasound probe and the vertical direction can be changed as needed, as shown in FIG. 5, using medical ultrasound coupling gel for coupling. In this example, the high-intensity focused ultrasound probe used is a single array element probe with a center frequency of 967 kHz and a focal length of 6.0 mm. In practical applications, high-intensity focused ultrasound probes with different center frequencies, focal lengths, and numbers of array elements can be freely chosen based on the requirements for treatment region size and intensity. The ultrasound probe is connected to a multi-channel ultrasound transmission and reception device.

(2) Transmission and Echo Data Collection of Multi-angle coherent plane waves. In this example, a linear array ultrasound probe with a center frequency of 15.6 MHz and 128 channels is used, transmitting 21 deflection angle plane waves per set. The echo signals are converted into voltage signals by the ultrasound transducer and processed by an analog signal amplifier and a filter, then subjected to analog-to-digital conversion and data storage. The sampling frequency for the analog-to-digital conversion is four times the center frequency of the ultrasound signal used for imaging. If the imaging region depth is d, the total length of the probe array is L, and the speed of ultrasound in soft tissue is c, then the shortest time interval between two ultrasound plane wave transmissions is $$t = 2 * \frac{\sqrt{d^2 + L^2}}{c},$$

if the number of inclined plane waves per set is N, then the maximum frame rate is $$K = \frac{1}{N * t}.$$

Different center frequencies, focal lengths, and numbers of array elements for the ultrasound imaging probe can be selected based on the requirements for treatment region size and intensity.

(3) Beamforming. In this example, the Delay And Sum (DAS) algorithm is used for beamforming, reconstructing images from stored echo signals. Then, the 21 images reconstructed from the echo signals of each set of 21 deflection angle plane waves are coherently compounded to produce a high-quality ultrasound B-mode image. The composite imaging frame rate in this embodiment is 500 Hz, with a sampling time of 0.4 s, resulting in a total of 200 compounded images. Parameters used for image reconstruction, such as imaging frame rate and sampling time, can be selected based on actual needs.

(4) Clutter filtering to obtain microvascular blood flow images. In this example, singular value decomposition is used for clutter filtering. S(x, z, t) is a three-dimensional spatio-temporal matrix of size ($n_x \times n_z \times n_t$), representing the information of 200 coherently compounded images, where x=880, z=128, t=200. This three-dimensional matrix S(x, z, t) is transformed into a two-dimensional matrix form Y of size ($n_x \times n_z \times n_t$), and then singular value decomposition is performed on it as shown in equation (1):

$$Y = U * \sum * V^T \quad (1)$$

where Σ is a diagonal matrix of dimensions ($n_x \times n_z$, $n_t$) with its diagonal entries being the singular values of Y. U and V are orthogonal unit matrices of dimensions ($n_x \times n_z, n_x \times n_z$) and ($n_t$, $n_t$) respectively, whose columns vectors correspond to the spatial and temporal singular vectors of Y.

After decomposing the 200-frame image matrix, singular values are arranged from largest to smallest. Larger singular values correspond to tissue signals, and smaller ones correspond to noise signals, with intermediate singular values representing dynamic blood flow signals. Low and high threshold values ($n_1$, $n_2$) are set to extract dynamic blood flow signals, in this example, n_1=20, n_2=180. By calculating according to equation (2), clutter filtering is achieved to obtain microvascular blood flow images:

$$S_{mbrain}(x, z, t) = \sum_{i=n_1}^{i=n_2} \lambda_i * U_i(x, z) * V_i(t) \quad (2)$$

where $U_i(x, z)$ and $V_i(t)$ represent the column vectors in matrices U and V corresponding to the singular value $\lambda_i$.

Figures 15, 16:
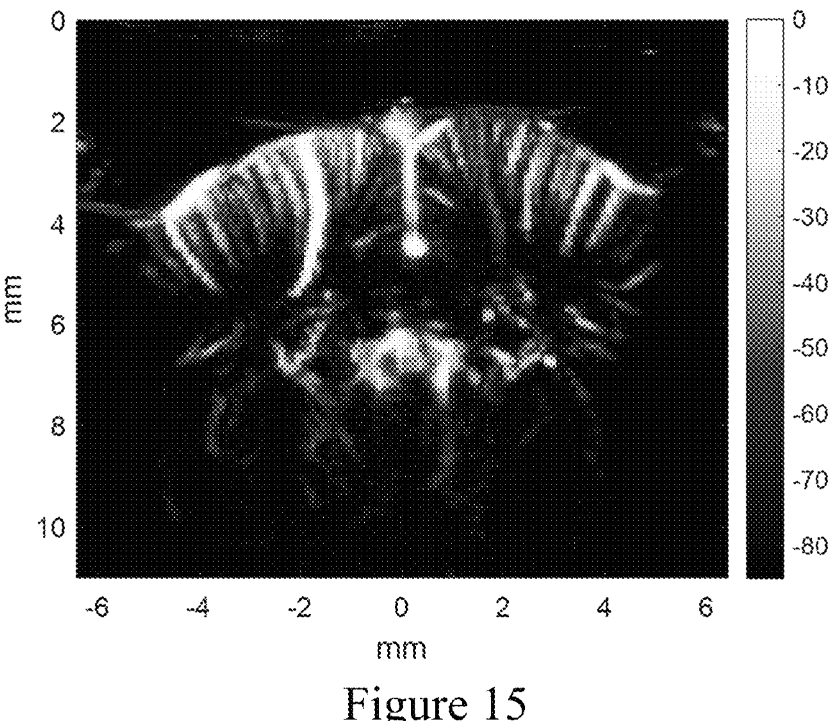
FIG. 15 is a two-dimensional image of ultrafast ultrasound power Doppler microvascular blood flow after pre-treatment clutter filtering in Example 2 for treating brain lesions in rats.
FIG. 16 is a two-dimensional image of ultrafast ultrasound power Doppler microvascular blood flow after treatment of the same region of the rat brain as in FIG. 15 in Example 2.
Figure 17:
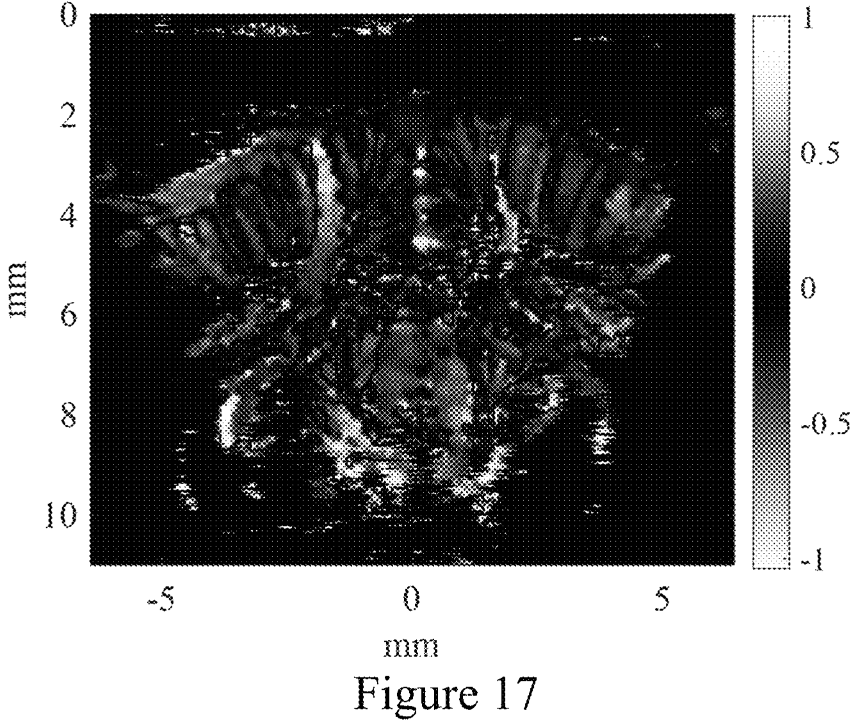
FIG. 17 is a two-dimensional image of ultrafast ultrasound color Doppler microvascular blood flow after pre-treatment clutter filtering in Example 2 for treating brain lesions in rats.

The dynamic blood flow signals extracted after clutter filtering are processed through orthogonal demodulation, frequency shift analysis, modulation, logarithm, and contrast adjustment, resulting in pre-treatment power Doppler 2D imaging results as shown in FIG. 15 and color Doppler 2D imaging results as shown in FIG. 17. FIGS. 15 and 17 can clearly display the microvascular blood flow images of the rat brain before the high-intensity focused ultrasound treatment.

Figure 19:
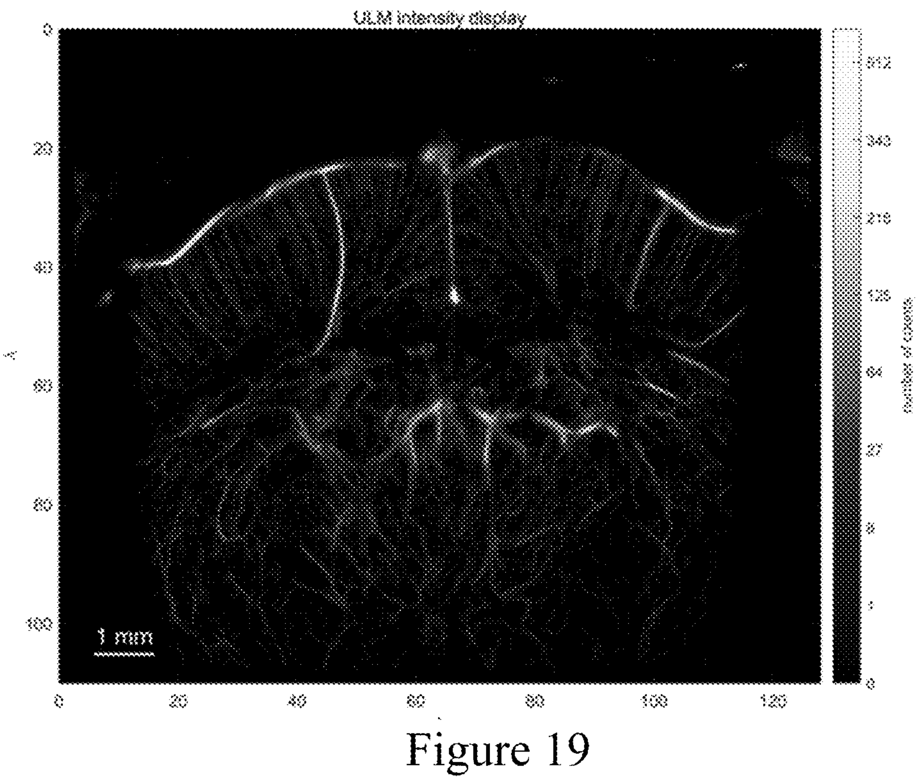
FIG. 19 is a super-resolution ultrasound localization microscopy blood flow density image after pre-treatment clutter filtering in Example 2 for treating brain lesions in rats.
Figure 21:
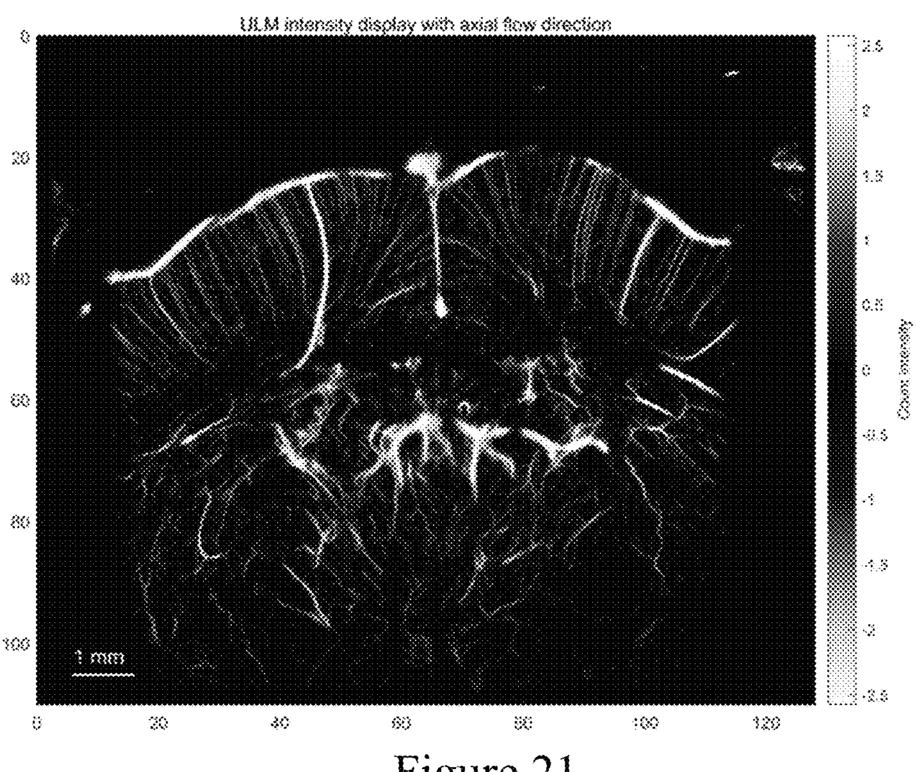
FIG. 21 is a super-resolution ultrasound localization microscopy blood flow direction image after pre-treatment clutter filtering in Example 2 for treating brain lesions in rats.
Figure 23:
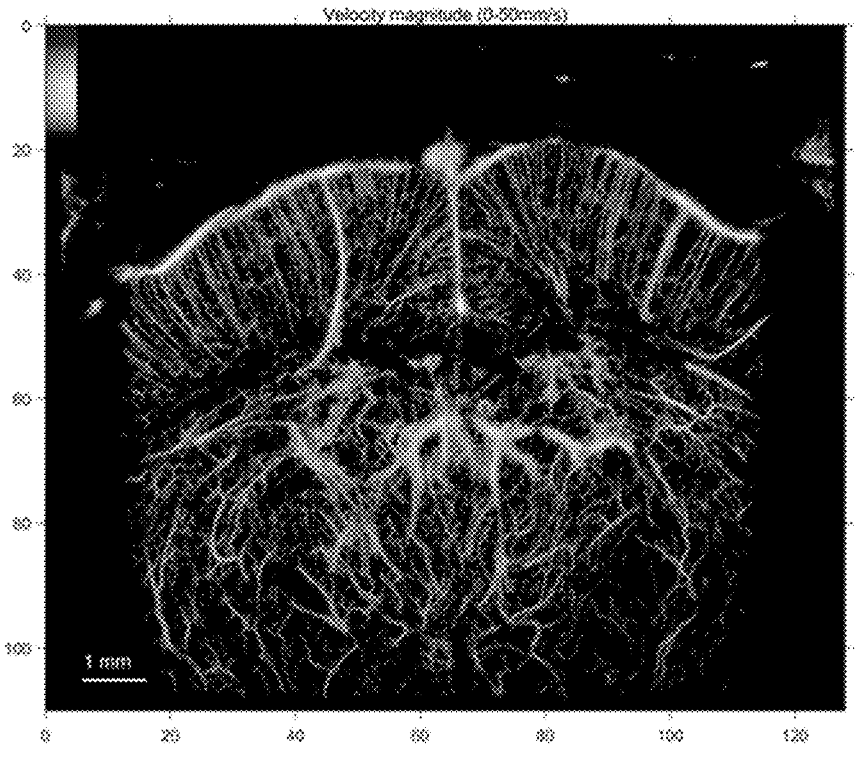
FIG. 23 is a super-resolution ultrasound localization microscopy blood flow velocity image after pre-treatment clutter filtering in Example 2 for treating brain lesions in rats.

(5) Super-resolution Ultrasound imaging. Ultrasound tracers are injected into the rat's bloodstream via venous injection. The process from (2) to (4) is repeated, with the transmission of plane waves at 5 different angles, the composite imaging frame rate is 1000 Hz, and the sampling time is 0.6 s, yielding 600 images per second after compounding. Orthogonal demodulation of the dynamic blood signal extracted after clutter filtering yields the orthogonal component IQ. The low and high threshold values for clutter filtering are set to $n_1$=30 and $n_2$=500, respectively, allowing for the extraction of images where tissue signals are separated from ultrasound tracers. Tracer localization identifies the center point of each ultrasound tracer using a radially symmetric localization method. After beamforming, the intensity value of an ultrasound tracer is radially symmetrical around its maximum value, where the gradient of intensity always points towards this maximum. This method locates the center by minimizing the distance from the center to the equipotential line (orthogonal to the gradient). After identifying the centers of ultrasound tracers, tracking them from frame to frame reveals their trajectories. The Kuhn-Munkres algorithm based on the Hungarian method is used for tracking ultrasound tracers, calculating the distance between each ultrasound tracer and all tracers in the next frame to minimize the total distance and connect all tracer positions to form trajectories. Finally, pre-treatment blood flow density images based on the number of ultrasound tracers as shown in FIG. 19, blood flow density images distinguishing upward and downward flows as shown in FIG. 21, and blood flow velocity images as shown in FIG. 23 are obtained. These images in FIGS. 19, 21, and 23 can display the microvascular blood flow images of the rat's brain before the high-intensity focused ultrasound treatment with high resolution.

Figures 29A, 29B:
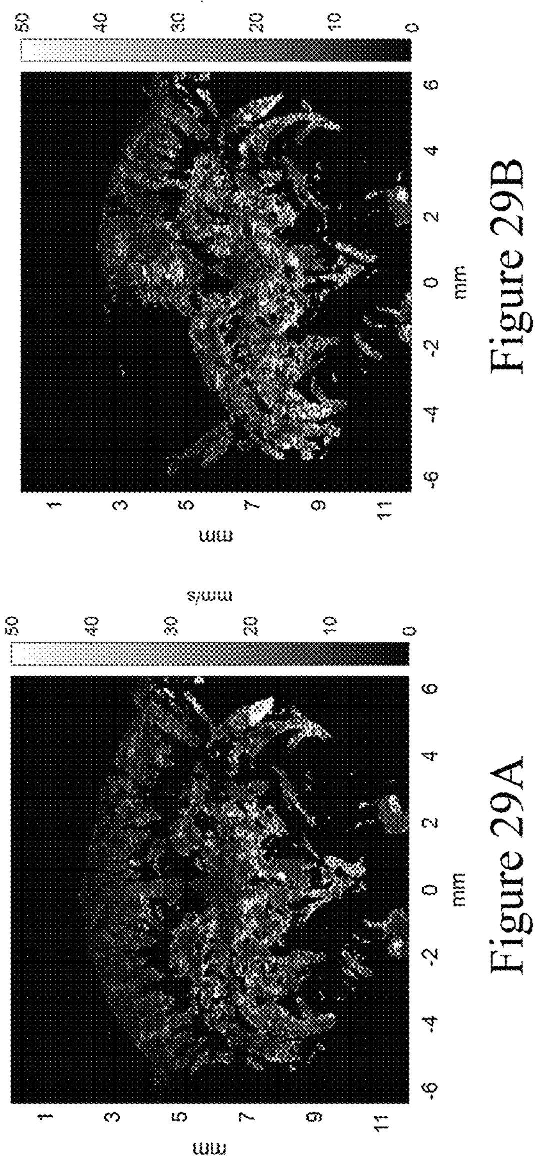
FIG. 29A is a pre-treatment example blood flow velocity distribution map.
FIG. 29B is a post-treatment example blood flow velocity distribution map.

Relevant blood flow vessel parameters extraction includes: FIGS. 29A and 29B show the schematic of blood flow velocity measurement results, wherein FIG. 29A displays the distribution of blood flow velocity in vessels before treatment, and FIG. 29B displays the distribution of blood flow velocity in vessels after treatment. The grayscale values correspond to the blood flow velocity in vessels at different locations.

Figure 30:
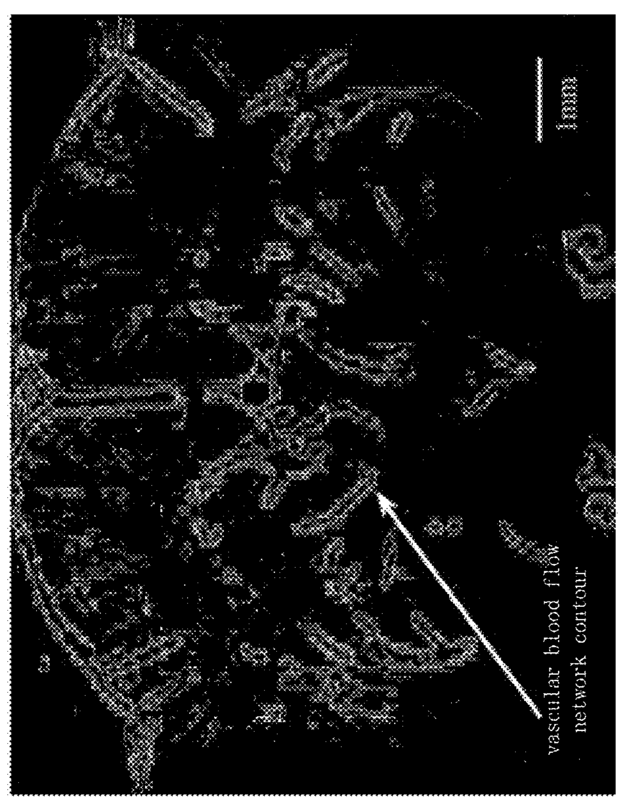
FIG. 30 is a result image of vascular blood flow contour extraction in example vascular blood flow images.

As shown in FIG. 30, contour extraction of the blood flow vessel images yields the vascular blood flow network contours. By calculating the ratio of the local vascular image area or volume to the total image area or space volume, the vascular radius and density index can be determined. Blood flow velocity images can be obtained through Doppler imaging processing. By integrating the blood flow velocity images over time, the blood flow volume index can be obtained.

(6) HIFU Treatment. In this embodiment, after the injection of ultrasound tracers and waiting for their excretion from the body, the high-intensity focused ultrasound probe is used to treat (or destroy) the left-sided brain tissue in the same plane as the ultrafast ultrasound imaging probe. Sinusoidal wave excitation is applied with a signal amplitude of 30 V, frequency of 967 kHz, and duration of 90 s, focusing 2 mm below the left cerebral cortex of the rat.

Figure 18:
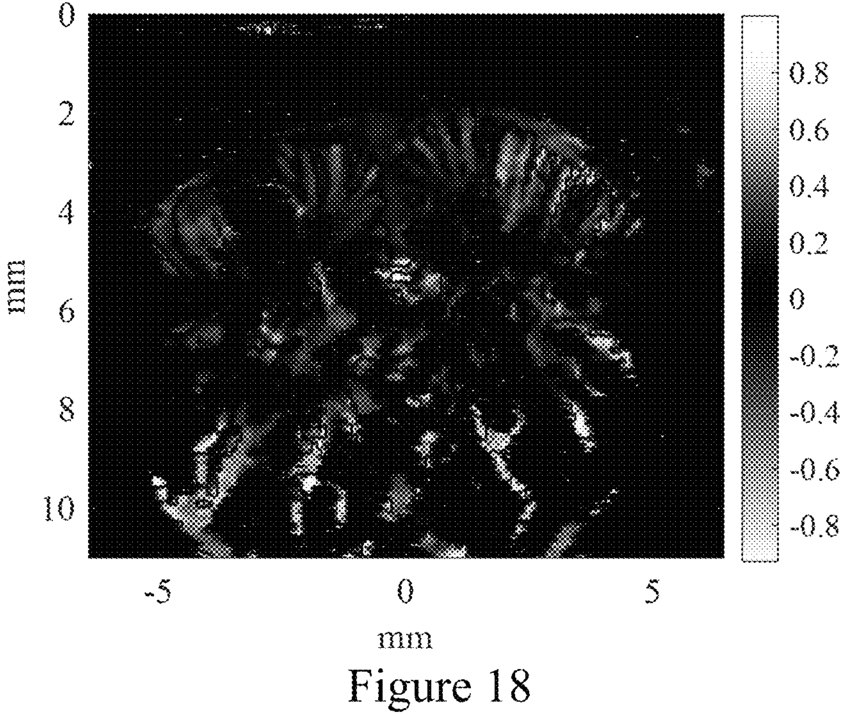
FIG. 18 is a two-dimensional image of ultrafast ultrasound color Doppler microvascular blood flow after treatment of the same region of the rat brain as in FIG. 17 in Example 2.

(7) Ultrafast Ultrasound imaging Post-HIFU Treatment. The process from (2) to (4) is repeated after one treatment to re-image the treatment region with ultrafast ultrasound imaging, yielding post-treatment power Doppler 2D imaging results as shown in FIG. 16, and color Doppler 2D imaging results as shown in FIG. 18. Based on these microvascular blood flow imaging results, corresponding vascular density, blood flow volume changes, and blood flow velocity index are determined to analyze the treatment effect (i.e., tissue destruction effect) in the treatment region. If the tissue destruction effect does not meet expectations, the high-intensity focused ultrasound treatment parameters may be adjusted and the treatment in (6) repeated.

Figure 20:
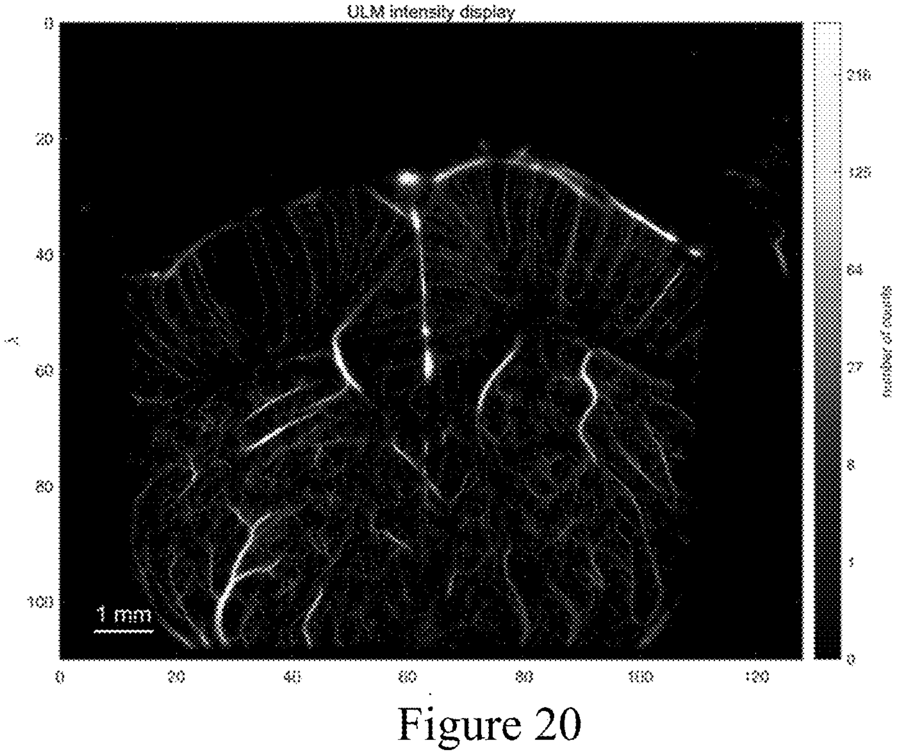
FIG. 20 is a super-resolution ultrasound localization microscopy blood flow density image after treatment of the same region of the rat brain as in FIG. 19 in Example 2.
Figure 22:
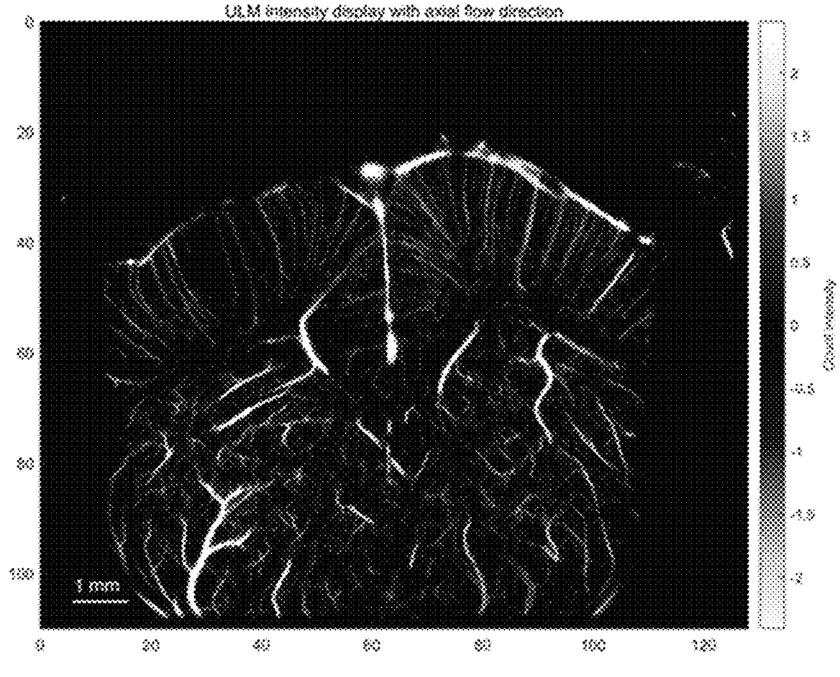
FIG. 22 is a super-resolution ultrasound localization microscopy blood flow direction image after treatment of the same region of the rat brain as in FIG. 21 in Example 2.
Figure 24:
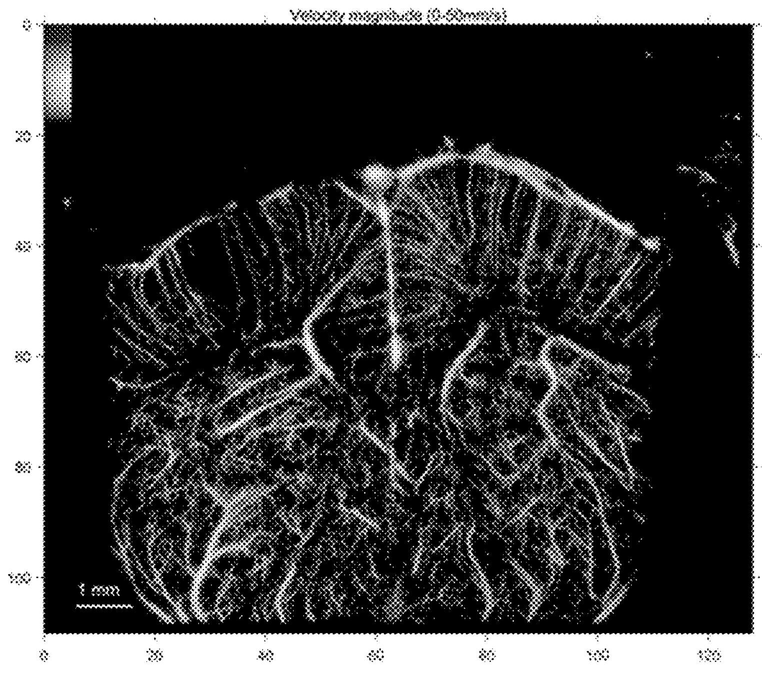
FIG. 24 is a super-resolution ultrasound localization microscopy blood flow velocity image after treatment of the same region of the rat brain as in FIG. 23 in Example 2.

(8) Super-resolution Ultrasound imaging Post-HIFU Treatment. The process in (5) is repeated after one treatment to re-image the imaging region with super-resolution ultrasound imaging, yielding post-treatment blood flow density images based on the number of ultrasound tracers as shown in FIG. 20, blood flow density images distinguishing upward and downward flows as shown in FIG. 22, and blood flow velocity images as shown in FIG. 24. Based on these super-resolution microvascular blood flow imaging results, corresponding indicators (such as vascular density, blood flow volume changes, and blood flow velocity) are determined to further analyze the treatment effect (i.e., tissue destruction effect) in the treatment region. If the tissue destruction effect does not meet expectations, the high-intensity focused ultrasound treatment parameters may be adjusted, and the treatment in (6) repeated.

Figure 25A:
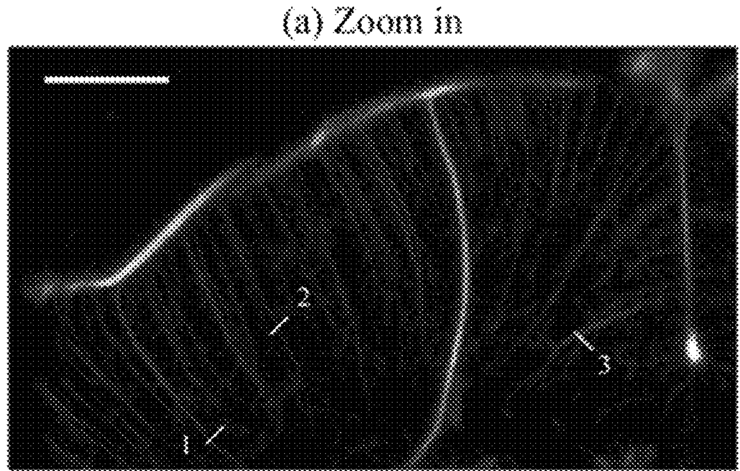
FIG. 25A is an image obtained by enlarging a part of FIG. 19.
Figure 25B:
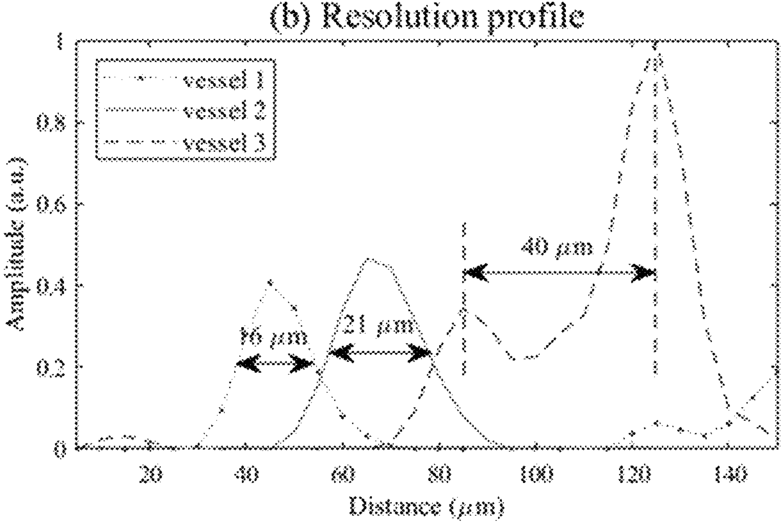
FIG. 25B is a graph showing the amplitude variation at the position indicated by the white horizontal line in FIG. 25A.

From the examples provided, it can be seen that the implementation of this invention enables precise treatment of lesions by obtaining microvascular blood flow images through the ultrafast ultrasound imaging unit and determining corresponding vascular density, blood flow volume changes, and blood flow velocity based on these images. Consequently, the treatment effects (i.e., tissue destruction effects) in the treatment region are calculated based on these indicators, and the treatment parameters of the focused ultrasound unit are adaptively adjusted based on the treatment effects. This allows for the precise treatment of lesions through the cooperation of the high-intensity focused ultrasound unit and the ultrafast ultrasound imaging unit. To better illustrate the effects of this invention, FIGS. 15 and 16, as well as FIGS. 17 and 18, were compared. It is observed that the post-treatment microvascular blood flow images obtained by the embodiments of this invention are clear and complete, allowing for accurate determination of corresponding vascular density, blood flow volume changes, and blood flow velocity. This ensures the reliability of the calculated treatment effects and the adjusted treatment parameters, demonstrating to a certain extent the feasibility and reliability of this invention's implementation. Furthermore, by comparing FIGS. 15, 16 with FIGS. 19, 20, it can be seen that the super-resolution microvascular blood flow image results are superior to those of general microvascular blood flow images, enhancing the resolution of the images. FIG. 25A shows an enlarged image of a selected region from FIG. 19, and the three curves in FIG. 25B correspond to the amplitude variations at three white lines in FIG. 25A, each passing through three vessels. From FIG. 25B, it is evident that the widths of vessels 1 and 2 are respectively 16 micrometers and 21 micrometers, indicating that super-resolution microvascular blood flow images can distinguish vessels within 20 micrometers. Vessel 3, having two bifurcations with a distance of 40 micrometers between them, can also be distinguished by super-resolution microvascular blood flow imaging. The super-resolution imaging results, as shown in FIGS. 19, 20, 21, 22, 23, and 24, can enhance the accuracy of indicators such as vascular density, blood flow volume changes, and blood flow velocity, thereby improving the accuracy of calculated treatment effects and adjusted treatment parameters.

It should be noted that in the application document of this patent, terms such as "first" and "second" are used only to distinguish one entity or operation from another, and do not necessarily imply any actual relationship or order between these entities or operations. Moreover, the terms "comprise," "include," or any other variations thereof are intended to encompass non-exclusive inclusion, such that a process, method, article, or device comprising a series of elements includes not only those elements but also additional elements not explicitly listed or inherently included for such process, method, article, or device. Unless specifically limited, the term "comprising a" does not exclude the possibility of including other identical elements in the process, method, article, or device that comprises the one element. When a behavior is performed according to a certain element in the application document of this patent, it means at least that the behavior is performed according to the element, including two situations: performing the behavior only according to the element, and performing the behavior according to the element and other elements. Expressions such as "multiple," "repeated," "various," etc., include 2, 2 times, 2 types, as well as 2 or more, 2 times or more, 2 types or more.

It should be noted that all documents mentioned in this specification are considered to be included in the disclosure of this application as a whole, so that they can be used as a basis for modification if necessary. In addition, it should be understood that the foregoing is merely exemplary of the principles and applications of the present specification and is not intended to limit the scope of the specification. Any modifications, equivalents, improvements, etc., made within the spirit and principles of one or more embodiments of this specification should be included within the scope of one or more embodiments of this specification.

The invention claimed is:

1. A focused ultrasound treatment system based on ultrasound imaging, comprising:

a focused ultrasound unit, configured to emit focused ultrasound waves to a lesion region for treatment;

an ultrasound imaging unit, configured to, after the treatment, emit imaging ultrasound waves to an imaging region and receive corresponding echoes, and based on the echoes, form a corresponding vascular blood flow image; and a region planning and parameter adjustment unit, configured to, based on the vascular blood flow image;

determine a vascular blood flow network contour of the lesion region;

determine a vascular density index, a blood flow velocity index, and a blood flow volume index of the lesion region based on the vascular blood flow image, and re-delineate the lesion region according to the vascular blood flow network contour;

score a lesion state of the re-delineated lesion region according to one or more of the vascular density index, blood flow velocity index, and blood flow volume index to obtain a scoring result, compare the scoring result with an expected result, and re-adjust the treatment parameters of the focused ultrasound unit based on a result of the comparison for the next treatment of the re-delineated lesion region, wherein the imaging region comprises the lesion region; and the vascular blood flow image is a microvascular blood flow image, wherein a spatial resolution of the microvascular blood flow image is less than or equal to a wavelength of the imaging ultrasound waves emitted by the ultrasound imaging unit, the spatial resolution and the wavelength each being measured in units of length.

2. The system of claim 1, wherein the ultrasound imaging unit emits ultrasound waves at a frame rate of ≥200 frames/s, and images at a frame rate of ≥50 frames/s.

3. The system of claim 1, wherein the region planning and parameter adjustment unit is further configured to determine the vascular blood flow network contour and blood flow direction within the re-delineated lesion region according to the vascular blood flow image, and to plan a treatment route based on the vascular blood flow network contour and the blood flow direction for the next treatment of the re-delineated lesion region by the focused ultrasound unit.

4. The system of claim 1, wherein, the system further comprises an image input unit and an image fusion unit; wherein, the image input unit is configured to acquire registration reference images and output them to the image fusion unit; the image fusion unit is configured to register and fuse the vascular blood flow image and the registration reference image to obtain a registered and fused image; and, the region planning and parameter adjustment unit is further configured to, based on the registered and fused image, re-delineate the lesion region and re-adjust the treatment parameters of the focused ultrasound unit for the next treatment of the re-delineated lesion region.

5. The system of claim 4, wherein the region planning and parameter adjustment unit is further configured to determine the corresponding vascular blood flow network contour and the respective vascular density index, blood flow velocity index, and blood flow volume index based on the registered and fused image, and to re-delineate the lesion region according to the vascular blood flow network contour and to score the lesion state of the re-delineated lesion region according to one or more of the vascular density index, blood flow velocity index, and blood flow volume index, compare the scoring result with an expected result, and re-adjust the treatment parameters of the focused ultrasound unit based on the comparison result for the next treatment of the re-delineated lesion region.

6. The system of claim 5, wherein the region planning and parameter adjustment unit is further configured to determine the vascular blood flow network contour and the blood flow direction within the re-delineated lesion region based on the registered and fused image, and to plan a treatment route based on the vascular blood flow network contour and the blood flow direction for the next treatment of the re-delineated lesion region by the focused ultrasound unit.

7. The system of claim 4, wherein the registration reference image is one or more of the following:

a B-mode image, a computed tomography (CT) image, a positron emission tomography (PET) image, a magnetic resonance imaging (MRI) image, an X-ray CT image, an MRI image with contrast agents, and a vascular image obtained from X-ray CT scans with contrast agents or MRI with contrast agents.

8. The system of claim 1, wherein the region planning and parameter adjustment unit is further configured to:

binarize the vascular blood flow image to obtain the vascular blood flow network contour; calculate the blood flow velocity index by using a quotient of a length of the tracer trajectory of a tracer in the blood vessel and a time taken by the tracer to move along the trajectory, or to directly obtain the blood flow velocity index from a power Doppler vascular blood flow image or a color Doppler vascular blood flow image;

based on the vascular blood flow network contour, determine central position points S(x, y) of each blood vessel vascular blood flow within the vascular blood flow network contour and obtain the vascular blood flow radius r(x, y) at each central position point S(x, y), and calculate the blood flow volume index using the formula $Q=\Sigma_{S(x,y)}v(x, y)*\pi r(x, y)^2$; and calculate the vascular density index by using a quotient of the region of the blood vessel vascular blood flow image formed by the vascular blood flow network contour and a current imaging image region, or a quotient of the volume of the blood vessel vascular blood flow image formed by the vascular blood flow network contour and a current imaging space volume.

9. The system of claim 1, wherein the ultrasound imaging unit is further configured to, after the treatment, emit imaging ultrasound waves to the imaging region and receive corresponding echoes, and based on the echoes, form a corresponding B-mode image, and obtain the vascular blood flow image based on the B-mode image.

10. The system of claim 9, wherein the ultrasound imaging unit is further configured to perform clutter filtering on the B-mode image, followed by positioning and tracking of either red blood cells or tracers within the clutter-filtered B-mode image, and based on the results of positioning and tracking, reconstruct the vascular blood flow image within the B-mode image to obtain a corresponding super-resolution vascular blood flow image, wherein the tracer is introduced into the vascular blood flow via venous injection after each treatment.

11. The system of claim 9, wherein the ultrasound imaging unit is further configured to perform clutter filtering, orthogonal demodulation, and frequency shift analysis on the B-mode image to obtain a corresponding power Doppler vascular blood flow image or a color Doppler vascular blood flow image.

12. The system of claim 1, wherein a cycle of sequential operations of the focused ultrasound unit, the ultrasound imaging unit, and the region planning and parameter adjustment unit constitutes a treatment cycle, and each treatment phase comprises a plurality of treatment cycles of iterations;

the ultrasound imaging unit is further configured to, before the treatment in the first treatment cycle of each treatment phase, emit imaging ultrasound waves to the imaging region and receive corresponding echoes, and based on these echoes, form a corresponding B-mode image, and obtain a vascular blood flow image based on the B-mode image; and, the region planning and parameter adjustment unit is further configured to delineate the corresponding initial lesion region and set the initial treatment parameters for the focused ultrasound unit based on the vascular blood flow image.

13. The system of claim 12, wherein the system further comprises an image fusion unit;

the ultrasound imaging unit, before the treatment in the first treatment cycle of each treatment phase, emits imaging ultrasound waves to the imaging region and receives corresponding echoes, and based on these echoes, forms a corresponding B-mode image, and obtains a vascular blood flow image, the image fusion unit registers and fuses this vascular blood flow image with a registration reference image from the image input unit to obtain a registered and fused image, the region planning and parameter adjustment unit delineates the corresponding initial lesion region and sets the initial treatment parameters for the focused ultrasound unit based on the registered and fused image.

14. The system of claim 1, wherein the treatment parameters comprises the focal length, focal intensity, focal spot size, emission frequency, emission power, duty cycle, and treatment duration of the focused ultrasound.

* * * * *